United States Patent [19]
Yamanaka et al.

[11] Patent Number: 5,919,422
[45] Date of Patent: Jul. 6, 1999

[54] TITANIUM DIOXIDE PHOTO-CATALYZER

[75] Inventors: Osamu Yamanaka, Nishikasugai-gun; Tadanobu Iwasa, Ichinomiya; Makoto Tamaki, Iwakura; Kazuhiro Sakai, Yoro-gun; Hisao Yamaguchi, Ichinomiya, all of Japan

[73] Assignee: Toyoda Gosei Co., Ltd., Aichi, Japan

[21] Appl. No.: 08/687,667

[22] Filed: Jul. 26, 1996

[30] Foreign Application Priority Data

| Jul. 28, 1995 | [JP] | Japan | 7-192819 |
| Jul. 28, 1995 | [JP] | Japan | 7-192821 |
| Jul. 28, 1995 | [JP] | Japan | 7-192829 |
| Jul. 31, 1995 | [JP] | Japan | 7-195572 |
| Jul. 31, 1995 | [JP] | Japan | 7-195573 |
| Jul. 31, 1995 | [JP] | Japan | 7-195576 |
| Oct. 2, 1995 | [JP] | Japan | 7-255331 |
| May 20, 1996 | [JP] | Japan | 8-124764 |

[51] Int. Cl.$^6$ ............................................. A62B 11/00
[52] U.S. Cl. ........................... 422/121; 422/122; 96/224
[58] Field of Search .................. 422/121, 124, 422/122; 96/224

[56] References Cited

U.S. PATENT DOCUMENTS

| 4,259,103 | 3/1981 | Malek et al. | 71/67 |
| 4,874,671 | 10/1989 | Tahara et al. | 428/447 |
| 4,954,465 | 9/1990 | Kawashima et al. | 502/5 |
| 5,243,204 | 9/1993 | Suzuki et al. | 257/77 |
| 5,393,993 | 2/1995 | Edmond et al. | 257/77 |

FOREIGN PATENT DOCUMENTS

| 0 614 682 | 9/1994 | European Pat. Off. . |
| 0 630 679 | 12/1994 | European Pat. Off. . |

*Primary Examiner*—Donna C. Wortman
*Assistant Examiner*—Brenda G. Brumback
*Attorney, Agent, or Firm*—Pillsbury Madison & Sutro LLP

[57] ABSTRACT

A photo-catalyzer for deodorizing, cleaning, sterilizing, and water purifying operations includes a substrate, a titanium dioxide film disposed on the substrate and functioning as a photo-catalyst, and a light-emitting diode disposed adjacent to the titanium dioxide film and producing ultraviolet light having a wavelength from 360 to 400 nm onto the titanium dioxide film. The photo-catalyzer can be used in places where there is no sunlight because it is optionally provided with a light-emitting diode. The light-emitting diode does not require a large installation space because it is an extremely small light-emitting device. Hence, the photo-catalyzer has a compact structure and can be used easily anywhere, including small places. The substrate can be fabricated into a variety of useful appliances to take advantage of the strong oxidizing properties of the photo-catalyzer. Devices comprising a photo-catalyzer may be used for deodorizing, destroying or repelling microorganisms, and including undertaking air or water purification.

10 Claims, 18 Drawing Sheets

TITANIUM DIOXIDE PHOTO-CATALYZER

BACKGROUND OF THE INVENTION

1. Field of the Invention

The present invention relates to a photo-catalyzer which utilizes a photo-catalytic reaction by means of a photo-catalyst including, for instance, a titanium dioxide film. A photo-catalyzer according to the present invention is capable of cleaning and deodorizing, destroying or repelling micro-organisms, and including undertaking air or water (e.g., drinking water, beverage) purification.

2. Description of Related Art

A photo-catalytic reaction, especially a strong oxidizing catalytic reaction, is of recent interest to engineers. The photo-catalytic reaction can be effected by fine particles of photo-semiconductor material, for example titanium dioxide ($TiO_2$).

When a particulate photo-semiconductor substance, such as titanium dioxide, is irradiated by light having at least the band-gap energy of the photo-semiconductor material (i.e., when titanium dioxide is irradiated by ultraviolet light having a wavelength of 400 nm or less), electrons present in the valency electron band are excited to migrate to the conduction band. Thus, free electrons are generated in the conduction band, and at the same time positively-charged particles (i.e., positive holes) are generated in the valency band. These positive holes and free electrons move in the semiconductor particulates, and later recombine over time. However, when there exists air, water, or compounds and ions in the substance having a level width (i.e., the spread in energy of an unstable state, equal to the difference between the energies at which intensity of emission or absorption of particles is one-half maximum value) lower than the energies of the positive holes and free electrons on the surface of the particulates, the positive holes and free electrons migrate into the compounds and ions by way of the particulate surface.

As a result, the positive holes directly oxidize the compounds and ions present on the particulate surfaces, or produce hydroxide-group radicals, one form of activated oxygen. The free electrons cause reduction reactions; mainly to reduce oxygen to reactive oxygen species, i.e., the free electrons add to oxygen to produce oxygen species having an oxidizing capability. Thus, when light is irradiated onto the fine particulates of photo-semiconductor, the fine particulates form an oxidative activated surface to act as a catalyst for the decomposition, or the like, of organic compounds. These operations of photo-semiconductor fine particulates are described in an article "Photo-related Catalytic Chemistry" in "KAGAGU SOSETSU (Chemistry Outline)", a Japanese quarterly magazine, No. 23, 1994.

Among photo-semiconductors, titanium dioxide exhibits an extremely high oxidizing catalytic action when used in fine particulate form. Titanium dioxide is also superb in terms of stability and safety. Many applications of titanium dioxide are known. Among known applications, titanium dioxide may be processed to a fine powder, and the fine powder may be applied as a film on a surface of a substrate to constitute a photo-catalyst. When the photo-catalyst is irradiated by ultraviolet light, it exhibits a high oxidizing capability which can be utilized to decompose organic compounds, etc.

Hollow glass beads, coated with a photo-catalyst comprising a titanium dioxide film, could be used as an agent for decomposing crude oil spilled on the sea. The crude oil deposited on the surface of the glass beads is decomposed by the strong oxidizing catalytic action of titanium dioxide which is activated by the ultraviolet component of sunlight.

Photo-catalysts, such as titanium dioxide, could be used to deodorize or destroy smells in indoor air, to destroy or repel bacteria in indoor air, or to decompose dirt-like cigarette tar or oil films. In these applications, the photo-catalyst is activated by utilizing ultraviolet radiation contained in natural light or light emitted from fluorescent lamps. The oxidizing catalytic action of the activated photo-catalyst is utilized to decompose odor compounds, such as mercaptan, or organic compounds, such as cigarette tar, or to destroy micro-organisms, such as fungi or bacteria, or to inhibit micro-organisms from growing.

Sunlight or fluorescent lamps have limitations when used as a source of ultraviolet light to activate a photo-catalyst comprising a titanium dioxide film, or the like. Accordingly, the photo-catalyst cannot be used where no sunlight shines or where no large-capacity fluorescent lamp can be provided to activate the photo-catalyst.

SUMMARY OF THE INVENTION

The present invention has been developed in order to improve the utility and the performance of a photo-catalyzer incorporated into a variety of devices. It is therefore an object of the present invention to provide a photo-catalyzer which is handy to use, and whose photo-catalyst comprises, for example, a titanium dioxide film that can be effectively irradiated by ultraviolet light.

A first aspect of a photo-catalyzer according to the present invention comprises:

a substrate;

a titanium dioxide film disposed on the substrate, and acting as a photo-catalyst; and a light-emitting diode disposed adjacent to the titanium dioxide film, and irradiating ultraviolet light having a wavelength from 360 to 400 nm onto the titanium dioxide film.

In the first aspect of the present photo-catalyzer, the titanium dioxide film acting as a photo-catalyst is disposed on a surface of the substrate where it contacts a fluid, such as air or water, to be subjected to the catalytic action. When the particle diameter of titanium dioxide forming the titanium dioxide film is sufficiently small, the titanium dioxide exhibits a high photo-catalytic action due to the "quantum size" effect, etc. Accordingly, it is preferred to form the titanium dioxide film as a transparent film in a thickness from 0.05 to 0.3 $\mu$m, more preferably from 0.1 to 0.2 $\mu$m, by coating a titanium dioxide colloid on a surface of the substrate and calcining it. Moreover, it is preferred to laminate the thus formed films as a laminated film. In addition, it is possible to form the titanium dioxide film by a physical vapor deposition (PVD) process, a chemical vapor deposition (CVD) process, or the like.

The photo-catalyzer according to the first aspect is provided with a light-emitting diode which produces light having a wavelength from 360 to 400 nm (i.e., ultraviolet light). Accordingly, the photo-catalyzer can be used where the photo-catalyzer is not subjected to sunlight.

The light-emitting diode is not only a small light-emitting device, but also can be operated at low voltage. Consequently, it can be operated by a dry-cell battery. Therefore, the light-emitting diode does not require a large space for its installation. Thus, the photo-catalyzer according to the first aspect of the invention can be used anywhere, including small places. In addition, the whole photo-catalyzer according to the first aspect can be downsized to a compact structure.

The photo-catalyzer according to the first aspect can be modified as follows. For example, it can be modified to a photo-catalyzer whose substrate is a photo-conductor including a transparent material, and whose light-emitting diode irradiates ultraviolet light onto the titanium dioxide film by way of the photo-conductor.

In the modified version of the photo-catalyzer according to the first aspect (hereinafter referred to as a "first modified version"), the photo-conductor is used to conduct ordinary light. Specifically, the photo-conductor is formed of transparent glass or transparent resin. The configuration of the photo-conductor can be a rod shape, a fiber shape, a plate shape, or a bulk shape. Note that the photo-conductor not only transmits light, but also conducts light, and that it conducts light virtually parallel to its surface. For instance, in the case of window glass, light is transmitted in a direction parallel to the surface of the window glass. Hence, window glass is not usually used as a photo-conductor. However, when a light source is disposed on one of the side-end surfaces of a glass plate and the light is introduced in a glass plate-extending direction (i.e., when light is passed through a glass plate substantially parallel to its surface), the glass plate can be used as a photo-conductor.

In the first modified version, the ultraviolet light from the light-emitting diode is sent via the photo-conductor to the titanium dioxide film applied to a surface of the photo-conductor. Accordingly, the ultraviolet light is less likely to leak and can be effectively irradiated onto the titanium dioxide film. As a result, it is possible to construct a photo-catalyzer which consumes less electric power.

Moreover, in the first modified version when the photo-conductor is used, the ultraviolet light traveling in the photo-conductor directly activates the photo-catalyst disposed on the surface of the photo-conductor, and the light-emitting diode is used as an ultraviolet source therefor. Therefore, by employing the photo-conductor and light-emitting diode, the first modified version can efficiently utilize the ultraviolet light, can be downsized, and can be conveniently used.

The first modified version can be further modified to a photo-catalyzer used as a muddler. For instance, the photo-conductor can comprise a of rod-shaped glass having a predetermined diameter, the photo-catalyzer can be applied to the surface of the rod, a case can be disposed at an end of the rod-shaped glass with a diameter larger than that of the rod-shaped glass, and the light-emitting diode and a battery for supplying an electric current to the light-emitting diode can be accommodated in the case. Note that the thus modified photo-catalyzer can be disposed in fluid media, in which air or water passes through the muddler to deodorize or decompose smells in the air or water, to destroy or repel bacteria therein, or to decompose organic substances therein.

The first modified version can be further modified to a photo-catalyzer used as a photo-decoration. For example, the substrate can be provided with a base, the photo-conductor can comprise a fiber and be fixed to the base at one of the opposite ends, the photo-catalyzer can be applied to the surface of the fiber, and the light-emitting diode can be accommodated in the base to transmit ultraviolet light through the photo-conductor and illuminate the photo-conductor. If such is the case, the light-emitting diode is required to emit visible light in addition to ultraviolet light.

The photo-catalyzer according to the first aspect can be modified in the following manner to a photo-catalyzer used as a bacteria-destroying and deodorizing apparatus. For instance, the substrate can include a housing having an accommodation chamber therein, the titanium dioxide film can be disposed on at least a part of an inner surface defining the accommodation chamber of the housing, and the light-emitting diode can be attached to the housing.

The modified version of the photo-catalyzer according to the first aspect (hereinafter referred to as a "second modified version" ) is provided with the titanium dioxide film which works as a photo-catalyst, and which is disposed on at least a part of an inner surface defining the accommodation chamber of the housing. When the titanium dioxide film receives the ultraviolet light from the light-emitting diode, the titanium dioxide film is activated to destroy or repel bacteria, or deodorize. Thus, the inside of the housing can always be kept odorless and clean. The accommodation space of the housing should not be reduced nor should the housing itself be enlarged, because the light-emitting diode is small.

In the second modified version, the ultraviolet light from the light-emitting diode activates the titanium oxide film constituting a photo-catalyst. The activated titanium oxide film destroys or repels bacteria, or deodorizes.

The light-emitting diode is not only a small light-emitting device, but also can be operated at low voltage. Consequently, it can be operated by a dry-cell battery to emit ultraviolet light. Therefore, the light-emitting diode does not require a large space for its installation, and can be accommodated and held in the housing with ease. Thus, it does not reduce the accommodation space in the housing at all.

The housing is an ordinary box which contains the accommodation chamber therein. The housing can be, for example, a medicine case, a cooler box, an enclosable soft-resin container, or a console box in automobiles. The housing can be preferably provided with a lid, but can also be without a lid. The housing can be fitted into an open-ended box, like a drawer, whose ceiling operates as a lid.

The titanium oxide film is disposed on at least a part of an inner surface defining the accommodation chamber of the housing. It can, however, cover all of the inner surfaces in their entirety.

The light-emitting diode is attached to the housing, and irradiates ultraviolet light onto the titanium oxide film which is disposed on at least an inner surface defining the accommodation chamber of the housing. The light-emitting diode can be fixed on an inner surface of a lid of the housing, and can irradiate the titanium oxide film which is disposed on a lower, inner surface of the accommodation chamber of the housing. The lower, inner surface opposes the inner surface of the lid on which the light-emitting diode is disposed. Moreover, a lid can turn off the supply of electricity to the light-emitting diode when the lid is opened, and can turn on the supply of electricity when the lid is closed. In addition, the electricity to be supplied to the light-emitting diode can be supplied by a battery which is accommodated in the housing, or by an external power source.

The photo-catalyzer according to the first aspect can be modified in the following manner to include a fan capable of purifying air. For instance, the substrate can include a rotary shaft, and a plurality of blades having opposite surfaces and held to the rotary shaft, disposed at equal intervals around the rotary shaft; and the titanium dioxide film can be disposed on one of the opposite surfaces of the blades.

It is the first feature of the modified version of the photo-catalyzer according to the first aspect (hereinafter referred to as a "third modified version") that the blades are provided with titanium dioxide film on one of the opposite surfaces. It is the second feature of the third modified version that a light-emitting diode is provided which irradiates ultraviolet light having a wavelength from 360 to 400 nm onto the titanium dioxide film.

In the third modified version, the titanium dioxide film (i.e.,the photo-catalyst) is disposed on one of the opposite surfaces of the blades which is most likely to contact air. Consequently, the third modified version can efficiently purify or deodorize a large amount of air. As a result, in the third modified version, the unit-surface-area air-purifying or air-deodorizing capability of the titanium dioxide film can be greatly increased.

In particular, when the third modified version is provided with a light-emitting diode for irradiating ultraviolet light onto the titanium dioxide film, a fan according to the third modified version can be incorporated into a wide variety of apparatuses. In addition, the fan should not be enlarged especially, but can be constructed as large as conventional fans, because the light-emitting diode is a small light-emitting device.

Note that, in the third modified version, the fan itself can be identical to conventional fans.

The third modified version can be further provided with a tubular guide. The guide surrounds the tip or outer edge of the blades.

When there exists a ultraviolet source other than the light-emitting diode, the third modified version does not require the light-emitting diode to provide ultraviolet light. When no other ultraviolet source is available, the third modified version requires its own source of ultraviolet light, such as a light-emitting diode. The light-emitting diode can preferably be integral to the fan and should efficiently irradiate ultraviolet light onto the titanium dioxide film disposed on the blades. In view of this, the light-emitting diode can preferably be disposed in the tubular guide which surrounds the circumferential path described by the end of the blades, or it can be disposed in the rotary shaft. Moreover, a bracket for exclusively fixing the light-emitting diode can be provided and can be disposed at a place where the light-emitting diode can irradiate ultraviolet light onto the titanium dioxide film most efficiently.

When the blades are made of a transparent material, the blades can be utilized as a photo-conductor, and the ultraviolet light of the light-emitting diode can be transmitted through the blades.

The titanium dioxide film can preferably be disposed on one of the opposite surfaces of the blades. The film can cover all of the opposite surface in its entirety, or can cover a surface of any other component part which is irradiated by ultraviolet light.

In the third modified version, it is preferred that, simultaneously with the activation of the fan, the light-emitting diode is turned on to produce ultraviolet light.

The third modified version can be applied to apparatuses which require fresh air delivery, for example, a fan for an air conditioner, a fan for introducing air into the interior of a house, or a home-use electric fan.

The photo-catalyzer according to the first aspect can be modified in the following manner to provide a novel air conditioner which can solve the problems associated with conventional air conditioners. Conventional air conditioners control the temperature and humidity of indoor air to make indoor air comfortable. However, conventional air conditioners do not cope with the odors of indoor air and smokes.

Conventional air conditioners allow indoor air to pass through as is, and recycle the air back to occupation spaces. Accordingly, when conventional air conditioners are kept out of service for a long period of time, micro-organisms (e.g., fungi or bacteria) gather in their ducts, or organic substances deposit and deteriorate on compartment walls to give off unpleasant odors.

A modified version of the photo-catalyzer according to the first aspect (hereinafter referred to as a "fourth modified version") can solve the problems of conventional air conditioners. For example, the fourth modified version is a photo-catalyzer which can be used with an air conditioner to provide a system capable of purifying air. This air conditioner system can not only purify indoor air efficiently, but also can remove unpleasant odors in a duct.

The fourth modified version is characterized in that the substrate is constituted as an air conditioning apparatus which comprises: a duct having an air inlet port and an air outlet port; a cooler disposed in the duct; a heater disposed therein; and an air blower provided with a fan, the fan having opposite surfaces; and a titanium dioxide film disposed in the duct and on a surface which contacts air flowing in the duct, and constitutes an air purifying and deodorizing apparatus together with a light-emitting diode. The thus constructed fourth modified version can be used with an air conditioner capable of purifying air.

In the fourth modified version, the titanium dioxide film is disposed in the duct and on a surface which contacts air flowing in the duct. The titanium dioxide film receives ultraviolet light produced by the light-emitting diode, thereby being activated. The activated titanium dioxide film oxidizes organic substances, like unpleasant odors, contained in air, thereby removing the organic substances and purifying the air. Alternatively, the air is purified by destroying or repelling micro-organisms such as fungi or bacteria. The purified air is discharged out of the air outlet port of the air conditioning apparatus.

The fourth modified version can also be constituted by incorporating the air purifying apparatus which effects the photo-catalytic action into the duct of ordinary air conditioners. Accordingly, it is possible to employ ordinary air conditioners per se to construct the constituent elements such as the duct, cooler, heater, and air blower. Ordinary air conditioners can be, for example, large-sized air conditioners for heating and cooling entire big buildings, medium-sized air conditioners in offices, or automobile air conditioners.

The duct forms a passage in which air to be cooled flows. It is provided with an air inlet port and an air outlet port.

The cooler is disposed in the duct to cool the air flowing in the duct. As for the cooler, an evaporator for evaporating a coolant of a compression-type cooling apparatus is suitable, or a heat exchanger for carrying out heat exchange between a cooling medium (e.g., a coolant) and air can be used.

The heater is disposed in the duct to heat the air flowing in the duct. As for the heater, an electric wire, like a nichrome wire, capable of generating heat and heating air, a burner capable of transmitting heat to air, or a heat exchanger for carrying out heat exchange between hot water and air are suitable.

The air blower takes air in through the duct via the air inlet port, and discharges the air via the air outlet port. Thus, it causes the air to flow. As for the air blower, air blowers which are provided with an ordinary propeller-type fan, or a sirocco-type fan may be employed.

Note that, depending on the application of the fourth modified version, it is possible to appropriately select and employ the appropriate configuration and size of the duct, and type, configuration and size of the cooler, heater and air blower.

In the fourth modified version, an inner surface of a duct, a surface of heat-dissipating or heat-absorbing fins of a heat exchanger, or a surface of a fan of an air blower can be employed as the surface which contacts the air flowing in the duct, and on which the titanium dioxide film is disposed. The inner surface of the duct has a relatively large surface area, and is convenient to apply a large-surface area titanium dioxide film. The surface of heat-dissipating or heat-absorbing fins of a heat exchanger always contact fresh air and allows efficient air purification. A fan of an air blower contacts a large amount of air per unit surface area and allows enhanced air-purifying efficiency.

Note that the surface on which the titanium dioxide film is disposed is not limited to an inner surface of constituent elements of ordinary air conditioners, or an external surface thereof. For instance, the surface can be a surface of a honeycomb-shaped support which is disposed in the duct. The honeycomb-shaped support herein means a honeycomb-shaped construction which is provided with a plurality of through bores disposed parallel to each other. As for the honeycomb-shaped support, ceramic and metallic honeycomb-shaped supports can be made.

When there is a possibility of generating unpleasant odors in the duct from organic substances, it is preferred that the titanium dioxide film is disposed downstream with respect to the source of unpleasant odors in the duct.

In the fourth modified version, the light-emitting diode is securely disposed at a place where it can irradiate ultraviolet light onto the titanium dioxide film. When required, a plurality of the light-emitting diodes can be utilized. Moreover, it is preferred that, simultaneously with the activation of the air conditioner, the light-emitting diode can be turned on to produce ultraviolet light.

The fourth modified version of the photo-catalyzer can be used in large buildings and halls, offices, homes, or automobiles which require purified or deodorized air.

In the fourth modified version, the light-emitting diode produces ultraviolet light to activate the titanium dioxide film. The strong oxidizing action of the activated titanium dioxide film decomposes and removes the unpleasant-odor components and smoke components contained in the air flowing in the duct, and thereby the air is purified. Also, micro-organisms such as fungi or bacteria can be destroyed or repelled. Thus, in addition to the inherent functions of the air conditioner (e.g., the temperature and humidity control of air), purified air is discharged out of the air conditioner. As a result, the fourth modified version can establish a comfortable living space. Additionally, the light-emitting diode is an extremely small light-emitting device, and does not require a large space for its installation. Hence, the fourth modified version is not enlarged at all, but can be downsized to a compact structure.

The photo-catalyzer according to the first aspect can be modified in the following manner to an air purifying apparatus. In this modified version (hereinafter referred to as a "fifth modified version"), the substrate is formed as a honeycomb-shaped support having a plurality of through bores disposed parallel to each other, and the titanium dioxide film is disposed on an end surface of the honeycomb-shaped support and on an inner surface of cellular walls defining the through bores. Thus, the photo-catalyzer according to the first aspect can be used as an air purifying apparatus.

In the fifth modified version, the surface area of the titanium dioxide film is enlarged by disposing the titanium dioxide film on the inner surfaces of the honeycomb-shaped support, and the light-emitting diode is employed to irradiate ultraviolet light onto the titanium dioxide film. Thus, the fifth modified version is intended for downsizing air purifying apparatuses.

The honeycomb-shaped support of the fifth modified version has a honeycomb-shaped construction. Honeycomb-shaped supports for exhaust-gas-purifying catalysts can be used as is. As for the honeycomb-shaped support, ceramic honeycomb-shaped supports, and metallic honeycomb-shaped supports can be used. Ceramics are used as a material for making the ceramic honeycomb-shaped supports. Stainless steel foils are used as a material for making the metallic honeycomb-shaped supports. Both of the ceramic and the metallic honeycomb-shaped supports can be employed as the honeycomb-shaped support of the fifth modified version.

Note that honeycomb-shaped supports formed of other materials can be utilized as well. However, since the honeycomb-shaped support in the fifth modified version is subjected to a strong oxidizing action which results from the photocatalytic action of titanium dioxide, it is preferable to utilize a honeycomb-shaped support which is formed of a material having good oxidation resistance. Both of the ceramic and metallic honeycomb-shaped supports are superb in terms of oxidation resistance, and are especially suitable for the honeycomb-shaped support of the fifth modified version.

A light-emitting diode irradiates ultraviolet light onto the end surface of the honeycomb-shaped support. The ultraviolet light coming into the through bores is irradiated onto the titanium dioxide film which is disposed on the inner surface of the through bores. The ultraviolet light is less likely to reach the inside of the through bores. Consequently, the honeycomb-shaped support can have a relatively short axial length. Note that, when the ultraviolet light is irradiated onto both end surfaces of the honeycomb-shaped support, the axial length of the honeycomb-shaped should reasonably be twice as large as that of the case where the ultraviolet light is irradiated onto only one of the end surfaces of the honeycomb-shaped support.

The titanium dioxide film is disposed on an end surface of the honeycomb-shaped support, and on an inner surface of cellular walls defining the through bores. Note that the titanium dioxide film can cover all surfaces of the honeycomb-shaped support.

The titanium dioxide film can be disposed on the end surface and on the inner surface by a slurry immersion process which is carried out identically with the formation of a loading layer on catalysts. For instance, a slurry is prepared with a titanium dioxide powder and an appropriate liquid, such as water. A honeycomb-shaped support is immersed into the resulting slurry to deposit the slurry on the end surface and the inner surface of the honeycomb-shaped support. Thereafter, the honeycomb-shaped support is heated to evaporate the liquid, and, if required, it is calcined to form a titanium dioxide film.

Note that a tough titanium dioxide film can be formed by mixing a proper binder into the slurry. Since the binder is subjected to a strong oxidizing action, it is preferable to employ an inorganic binder, a fluorocarbon-resin-based binder, or a silicone-resin-based binder which exhibits high oxidation resistance.

The light-emitting diode irradiates ultraviolet light onto the end surface of the honeycomb-shaped support. The ultraviolet light naturally gets into the through bores of the honeycomb-shaped support, and is irradiated onto the inner surface of the cellular walls defining the through bores.

The light-emitting diode can be disposed in front or back of the honeycomb-shaped support by a predetermined distance away from the end surface thereof, or it can be disposed in front and back thereof by a predetermined distance away from the end surfaces thereof. A plurality of the light-emitting diodes can be employed, if desired.

When incorporating the fifth modified version into existing air conditioners, the fifth modified version is assembled in a duct of air conditioners. Then, the light-emitting diode is fastened in front or back of the honeycomb-shaped support by a predetermined distance away from the end surface thereof, or it is fastened in front and back thereof by a predetermined distance away from the end surfaces thereof. The incorporation is thus completed. Note that a tubular case can be prepared independently of existing ducts, that is the tubular case forms a passage through which air passes, and it can accommodate the honeycomb-shaped support and light-emitting diode according to the fifth modified version therein. In service, the fifth modified version accommodated in the tubular case can be disposed in a duct of an existing air conditioner.

When there is no air flow available, it is preferred that the fifth modified version is provided with an air blower to move air in the through bores of the honeycomb-shaped support.

In the fifth modified version, the light-emitting diode is powered by flowing an electric current therein when air flows in the through bores of the honeycomb-shaped support. The light-emitting diode irradiates ultraviolet light onto the titanium dioxide film to activate the oxidizing action. The oxidizing action of the activated titanium dioxide film purifies the air flowing in the honeycomb-shaped support.

The fifth modified version can be used inside of houses where purified air is required, and in a duct of air conditioners.

In the fifth modified version, the titanium dioxide film is disposed on the surfaces (e.g., the end surface and the inner surface) of the honeycomb-shaped support. The honeycomb-shaped support has a plurality of through bores, which are parallel to each other, and through which air flows. The honeycomb-shaped support is thus provided with cellular walls therein. An inner surface of the cellular walls defines the through bores, and has a wide surface area. Accordingly, the titanium dioxide film has a wide surface area, and thereby it can purify the air with increased efficiency. The honeycomb-shaped support does not cause a large pressure loss in the air flowing therethrough, nor does it present an obstacle to airflow.

The light-emitting diode produces ultraviolet light to activate the titanium dioxide film. The activated titanium dioxide film, loaded on the honeycomb-shaped support, decomposes and removes unpleasant-odor components and smoke components contained in the air being brought into contact with it, and thereby purifies air. The light-emitting diode is an extremely small light-emitting device, and does not require a large space for its installation. Hence, the photo-catalyzer according to the fifth modified version can be downsized to a compact structure.

In order to provide a photo-catalyzer which can be further downsized to a more compact structure, which can be placed at many locations with a high degree of freedom, and in which a photo-catalyst can be irradiated by ultraviolet light efficiently, the photo-catalyzer according to the first aspect can be modified as follows to comprise (hereinafter referred to as a "sixth modified version"):

a bulky support including fibers;

a photo-catalyst disposed on the bulky support; and a light-emitting diode disposed adjacent to the bulky support, and irradiating ultraviolet light having a wavelength from 360 to 400 nm onto the bulky support.

In the sixth modified version, the term, "bulky support", means a substrate which has been treated so that air spaces are developed therein to increase the bulkiness thereof. The fibers constituting the bulky support can preferably be formed of at least one member selected from the group of transparent glass and transparent resin.

Likewise, in order to accomplish the objectives of the sixth modified version, the photo-catalyzer according to the first aspect can be modified as follows to comprise (hereinafter referred to as a "seventh modified version"):

a porous support formed from a transparent material;

a photo-catalyst disposed on the porous support; and a light-emitting diode disposed adjacent to the porous support, and irradiating ultraviolet light having a wavelength from 360 to 400 nm onto the porous support.

In the sixth and seventh modified versions, the bulky support and the porous support enable the ultraviolet light to efficiently irradiate onto the photo-catalyst even when powered by a dry-cell battery, or the like. The sixth and seventh modified versions can be further downsized to a more compact structure, and can be placed at many locations with a high degree of freedom. Thus, the sixth and seventh modified versions can be utilized in a variety of applications, for example, deodorizing, sterilizing or repelling bacteria, and inhibiting contaminants.

The photo-catalyzer according to the first aspect, and a photo-catalyzer according to a second aspect described hereinafter utilize a photo-catalyst. The operation principle of the photo-catalyst will be detailed hereinafter. FIG. 1 is an illustration to explain the operating principles of a photo-catalyst which is utilized in the photo-catalyzers according to the first and second aspects.

In general, the photo-catalyst is believed to operate in the following manner as illustrated in FIG. 1. A particulate substance with photo-semiconductor properties, such as titanium dioxide ($TiO_2$), is irradiated by light having a band-gap (i.e., forbidden band) energy thereof or more. For instance, when titanium dioxide is irradiated by light having a wavelength of 400 nm or less (i.e., ultraviolet light), electrons ($e^-$) present in the valency electron band are excited optically to migrate to the conduction band. Thus, free electrons are generated in the conduction band, and at the same time particles charged positively (i.e., positive holes ($h^+$)) are generated in the valency band. These positive holes and free electrons move in the photo-semiconductor particulates, and recombine to disappear with time. However, when there exists an environment involving oxygen ($O_2$) or water ($H_2O$), the positive holes and free electrons migrate into that environment to produce highly active $HO_2$ radicals and HO radicals. The $HO_2$ radicals and HO radicals easily decompose a variety of harmful substances and bad-smelling substances present in air or water, and make them harmless. Thus, when the photo-catalyst is irradiated by sunlight, which has an ultraviolet component, the photo-catalyst acts as a medium which carries out the decomposition, or the like, of organic compounds.

Among photo-catalysts, titanium dioxide exhibits a remarkably high oxidizing catalytic action when formed as photo-semiconductor particulates. Further, titanium dioxide not only exhibits a high photo-catalytic reactivity, but also it is stable chemically and keeps the photo-catalytic reaction going continuously or semi-permanently. Furthermore, titanium oxide is harmless to human bodies, and is accordingly superb in terms of safety. Hence, in the photo-catalyzers according to the first and second aspects, a fine powder of titanium oxide is formed into a film, etc. The film is applied to a substrate 11 to constitute a photo-catalyst 13, and its high oxidizing capability is utilized for the decomposition, or the like, of organic compounds when the film is irradiated by ultraviolet light.

For example, sunlight shining into the inside of houses or the passenger compartment of automobiles, and reflected light as well, can be used to activate the photo-catalyst 13. Consequently, the photo-catalyst 13 constitutes a reactive surface having a strong oxidizing power. Thus, the photo-catalyst 13 decomposes organic compounds, unpleasant-odor components, and organic substances, being brought into contact therewith, by means of the oxidizing catalytic reaction, or it destroys or inhibits from growing germs like fungi or bacteria. The organic compounds to be decomposed can be sulfur-including organic compounds, such as hydrogen sulfide and mercaptan, nitrogen-including organic compounds, such as trimethylamine and propylamine, and hydrocarbons, such as toluene and xylene. The unpleasant-odor components to be decomposed can be aldehydes or carboxylic acids, such as butyric acid and n-pentanoic acid. The organic substances to be decomposed can be cigarette tar. Therefore, the photo-catalyst 13 semi-permanently keeps purifying air in the inside of houses or the passenger compartment of automobiles, deodorizing, reducing germs, and inhibiting germs from growing.

A second aspect according to the present invention is a photo-catalyzer used as a bacteria-repelling and deodorizing apparatus, and comprises:

a substrate having opposite surfaces, and titanium dioxide exposed on one of the opposite surfaces of the substrate.

When the photo-catalyzer according to the second aspect further comprises an adhesive layer which is laminated on another of the opposite surfaces of the substrate, it can be posted on a wall of kitchens, bathrooms and lavatories which can be subjected to ultraviolet irradiation, or on furniture in order to purify ambient air and simultaneously inhibit germs from growing.

In the photo-catalyzer according to the second aspect, the titanium dioxide is exposed on one of the opposite surfaces of the substrate. The titanium dioxide operates as a strong oxidizing catalyst. Accordingly, organic substances adjacent to the titanium dioxide are subjected to a strong oxidizing action. In order to withstand the oxidizing action resulting from the titanium dioxide, it is preferred that a matrix or a binder for holding the titanium oxide is a highly oxidation-resistant substance. From this viewpoint, it is preferred that a substance for holding the titanium dioxide is an oxidation-resistant synthetic resin, such as a fluorocarbon resin or a silicone resin, or an oxidation-resistant inorganic adhesive, such as silicate or phosphate. Hence, it is preferred that the substrate is formed of an oxidation-resistant synthetic resin, such as a fluorocarbon resin or a silicone resin, or an oxidation-resistant inorganic adhesive, such as silicate or phosphate.

Considering the fact that it is necessary to provide the bacteria-repelling and deodorizing function on one of the opposite surfaces of the substrate only, the substrate can include a base layer having opposite surfaces; and a top layer laminated on one of the opposite surfaces of the base layer, and including a silicone resin, a fluorocarbon resin, or an inorganic substance involving a titanium dioxide powder therein. If such is the case, the base layer is protected from the strong oxidizing action of titanium dioxide. Therefore, as the base layer, it is possible to employ ordinary films, such as a polyester film, a vinylchloride film or a polyolefin film, which can be used as materials for preparing sheets.

The top layer can be formed integrally as a thin film on one of the opposite surfaces of the base layer. The thin film can be an oxidation-resistant synthetic resin, like a fluorocarbon resin or a silicone resin, in which a titanium dioxide powder is compounded. Moreover, the top layer can be formed by fixing a titanium dioxide powder with an inorganic binder.

Titanium dioxide can be formed as a thin film by a physical vapor deposition process, or a chemical vapor deposition process. If such is the case, no binder is required. However, a base layer for holding a titanium-dioxide vapor-deposition film is required to be highly oxidation-resistant. Accordingly, in order to prepare the substrate, the base layer can be formed of a fluorocarbon resin or a silicone resin, and a titanium-dioxide vapor-deposition film can be disposed on one of the opposite surfaces of the base layer. In particular, when a base layer should have exceptionally strong oxidation resistance, an inorganic cloth can be used as a base layer. The inorganic cloth can be knitted or woven with an inorganic fiber like a glass fiber. On the inorganic-cloth base layer, a titanium-dioxide vapor-deposition film can be formed, or a top layer can be formed by using a fluorocarbon resin or a silicone resin in which a titanium dioxide powder is compounded.

The adhesive layer is disposed on another of the opposite surfaces of the substrate. The adhesive layer can be formed of known sticky substances. Specifically, the adhesive layer can be formed of an unvulcanized rubber, a thermoplastic elastomer, or a vinyl acetal resin.

When the photo-catalyzer according to the second aspect is not in service, it is preferred that a protective layer cover the sticky layer to inhibit the sticky layer from functioning. During operation, the protective layer is removed and the photo-catalyzer according to the second aspect is disposed on a predetermined installation surface.

Ultraviolet light is needed to effectively activate the photo-catalyzer according to the second aspect. Note that sunlight contains an ultraviolet component for effectively operating the photo-catalyzer according to the second aspect, and that fluorescent lamps, like sterilizing lamps, also produce effective ultraviolet light.

If no appropriate ultraviolet source is available, it is possible to employ the same light-emitting diode as used in the photo-catalyzer according to the first aspect.

The photo-catalyzer according to the second aspect can be used readily, for instance, by bonding it on a wall of a room, a surface of furniture, or a blade surface of a fan. When it is irradiated by ultraviolet light, it effects a strong oxidizing action. Thus, it decomposes and removes the unpleasant-odor components and cigarette-smoke components contained in the ambient air, and its strong oxidizing action inhibits germs from being active. As a result, in places where the photo-catalyzer according to the second aspect is operational, no unpleasant odors are present, the surrounding air is purified, and ambient germs are decreased, thereby improving the environment.

The photo-catalyzer according to the second aspect can be modified in the following manner to a light-shielding apparatus for a vehicle. This modified version (hereinafter referred to as an "eighth modified version") is a photo-catalyzer used as a vehicle light-shielding apparatus, and comprises:

a substrate disposed at a predetermined position in a vehicle and oriented substantially in a plane, and including a heat-resistant material having a light-shielding property as a whole; and titanium dioxide disposed continuously in the plane of the substrate, and formed as a film.

The photo-catalyzer according to the second aspect can be modified in the following manner as a curtain for a vehicle. This modified version (hereinafter referred to as a "ninth modified version") is a vehicle curtain, and comprises:

a substrate disposed at a predetermined position in a vehicle and oriented substantially in a plane, and including a heat-resistant cloth; and titanium dioxide disposed continuously in a surface-wise direction on the substrate, and formed as a film.

The photo-catalyzer according to the second aspect can be modified in the following manner to a blind for a vehicle. This modified version (hereinafter referred to as a "tenth modified version") is a photo-catalyzer used as a vehicle blind, and comprises:

a substrate disposed at a predetermined position in a vehicle and oriented substantially in a plane, and including a plurality of slats, the slats disposed parallel to each other, and including a heat-resistant plate-shaped material having a substantially uninterrupted length; and titanium dioxide disposed continuously in a surface-wise direction on the slats, and formed as a film.

The eighth, ninth and tenth modified versions oxidize and decompose organic components, such as unpleasant odors and dirt dissipated in vehicles, to purify and sterilize the air in vehicles. At the same time, they purify and sterilize their substrates to keep them clean. Contrary to conventional air conditioners, they do not require an installation space which is prepared especially therefor, and they inherently possess the air-purifying function. As a result, not only do they improve the environment in vehicles, but also they can effectively provide an air-purifying function, etc., to vehicles. In particular, when the titanium dioxide film is prepared by calcination, the photo-catalyst comprises a highly reactive titanium dioxide film which includes an anatase-type crystalline structure, and is tightly applied onto one of the opposite surfaces of the substrate. Therefore, the photo-catalyst can effect the air purifying function, or the like, more effectively. Moreover, they can produce these advantages without increasing the number of component parts for constituting vehicles. In addition, they can keep the insides of vehicles well-serviced under natural conditions.

BRIEF DESCRIPTION OF THE DRAWINGS

A more complete appreciation of the present invention and many of its advantages will be readily obtained as the same becomes better understood by reference to the following detailed description when considered in connection with the accompanying drawings and specification, all of which form a part of the disclosure:

FIG. 33 is a cross-sectional view for illustrating major portions of a microphone in which a Nineteenth Preferred Embodiment of the present photo-catalyzer is built-in:

FIG. 35 is a front view for illustrating a clothing hanger in which a Twenty-first Preferred Embodiment of the present photo-catalyzer is built-in.

DETAILED DESCRIPTION OF THE PREFERRED EMBODIMENTS

Having generally described the present invention, a further understanding can be obtained by reference to the specific preferred embodiments which are provided herein for the purpose of illustration only and are not intended to limit the scope of the appended claims.

The specific preferred embodiments of the present photo-catalyzer will be hereinafter described with reference to the accompanying drawings.

First Preferred Embodiment

Figure 1:
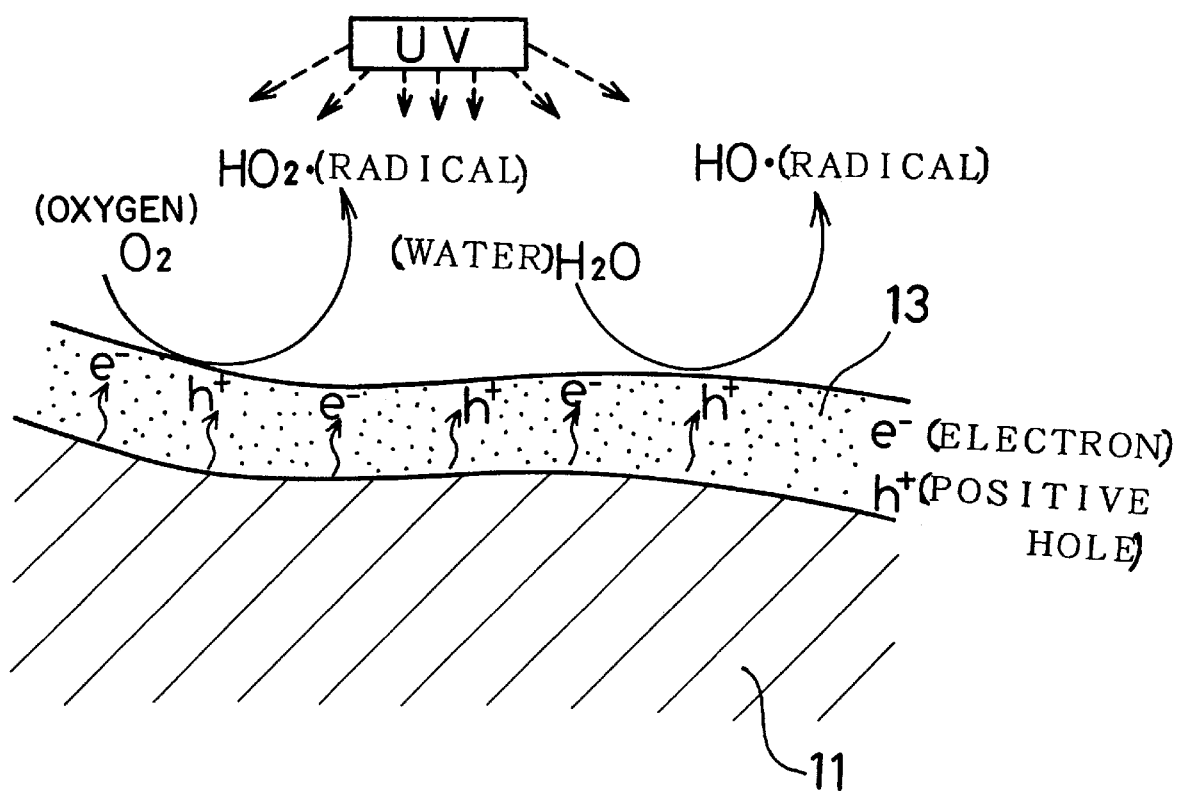
FIG. 1 is an explanatory diagram for illustrating the operation principle of a photo-catalyzer of the present invention.
Figure 2:
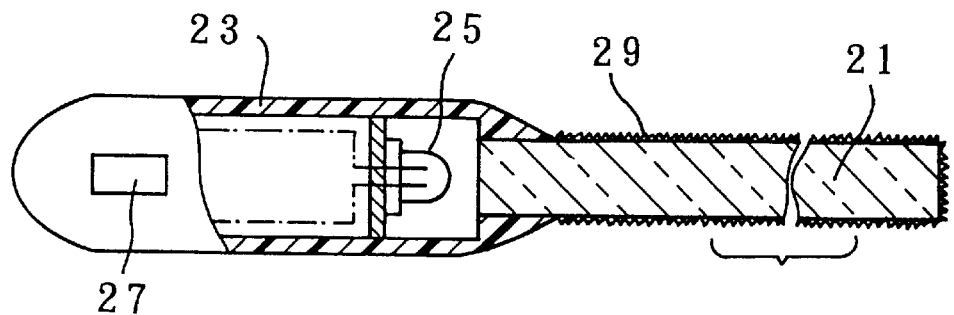
FIG. 2 is an overall view for illustrating a muddler according to a First Preferred Embodiment of the present photo-catalyzer which is partly depicted in cross-section.

FIG. 2 illustrates a First Preferred Embodiment of the present photo-catalyzer. This photo-catalyzer is constructed as a muddler (i.e., a stirrer). FIG. 2 illustrates the muddler partly in cross-section. This muddler comprises a glass rod 21, a case 23, a light-emitting diode 25, and a dry-cell battery (not shown). The glass rod 21 constitutes a photo-conductor. The case 23 is fixed at one of the opposite ends of the glass rod 21. The light-emitting diode 25 is fixed in the case 23 so as to face one of the opposite ends of the glass rod 21. The battery is accommodated in the case 23 coaxially with the light-emitting diode 25. The case 23 is provided with a switch 27 which turns on and off electricity supplied to the light-emitting diode 25. On the outer peripheral surface of the glass rod 21, there is disposed a titanium dioxide film 29. The titanium dioxide film 29 is vapor-deposited by a PVD process, and is semi-transparent pale yellow.

The light-emitting diode 25 is a small light-emitting device, and comprises a tip and a molded lens. The tip includes a gallium nitride (GaN)-based photo-semiconductor crystal having a p-n junction and emitting light. The molded lens encloses the tip therein, and gives the emitted light direction. The light-emitting diode 25 emits light (or electromagnetic waves) having a wavelength from 360 to 400 nm, namely, they emit intense blue light together with ultraviolet light.

Note that, in view of light-emitting efficiency and electricity consumption, it is preferred that the light-emitting diode 25 only produces light whose wavelength falls in a spectrum range from 360 to 400 nm only. In actual applications, contrary to semiconductor lasers, light-emitting diodes generally produce light whose wavelength spreads over at least 50 nm. Accordingly, it is difficult to provide a light-emitting diode capable of emitting light whose wavelength falls in a range from 360 to 400 nm only. Hence, in the First Preferred Embodiment, any light-emitting diode can be employed which emits light (or electromagnetic waves) with a sufficient ultraviolet component having a wavelength from 360 to 400 nm (e.g., GaN, SiC, ZnO, ZnS).

Moreover, it is preferred that the light-emitting diode 25 barely emits ultraviolet light harmful to the human body, for instance, the far ultraviolet (e.g., UV-B or UV-C) having a wavelength of 320 nm or less. Such a light-emitting diode 25 can construct a photo-catalyzer which is not harmful to the human body and can be used safely in daily-life applications.

On the other hand, light having a wavelength of 400 nm or more (i.e., visible light) is not harmful to the human body. Light-emitting diodes capable of producing visible light can be used without causing any problems. When such a light-emitting diode 25 is used, it is possible to tell that the light-emitting diode 25 is in operation. In addition, when such a light-emitting diode 25 emits visible light which exhibits bright and vivid colors, the light-emitting diode 25 can produce an illuminating or displaying effect. Note that, however, for light having a wavelength of 400 nm or less, light having a wavelength of about 380 nm produces a blurry background in dark purple, for example. Therefore, even when the light-emitting diode 25 emits light having a wavelength of 400 nm or less only, the emitted light is not black light completely, but is usually visible.

The muddler, the First Preferred Embodiment of the present photo-catalyzer, accommodates the dry-cell battery in the case 23. When the switch 27 is turned on to actuate the light-emitting diode 25 to emit light, the muddler produces intense blue light together with ultraviolet light having a wavelength from 360 to 400 nm. The ultraviolet light enters the glass rod 21 from one of the opposite-end surfaces, and travels down the glass rod 21. Some of the ultraviolet light leaks outside directly: through the side surface and the another opposite-end surface. The remaining ultraviolet light is refracted or reflected, and eventually is released through the side surface and the another opposite-end surface. The ultraviolet light thus released from the side surface and the another opposite-end surface irradiates the titanium dioxide film 29, and produces an oxidizing reactive surface on the titanium dioxide film 29.

The pale blue visible light is also released from the side surface and the another opposite-end surface, and can be recognized in dark places.

When water is stirred by using the muddler with the activated oxidizing surface, organic substances are decomposed in the water. The muddler thus purifies the water.

The First Preferred Embodiment of the present photo-catalyzer is utilized as a muddler. Note that, however, a photo-catalyzer of identical construction can be used for deodorizing, destroying or repelling bacteria, dirt prevention, air purification, or drinking-water or beverage purification.

Second Preferred Embodiment

Figure 3:
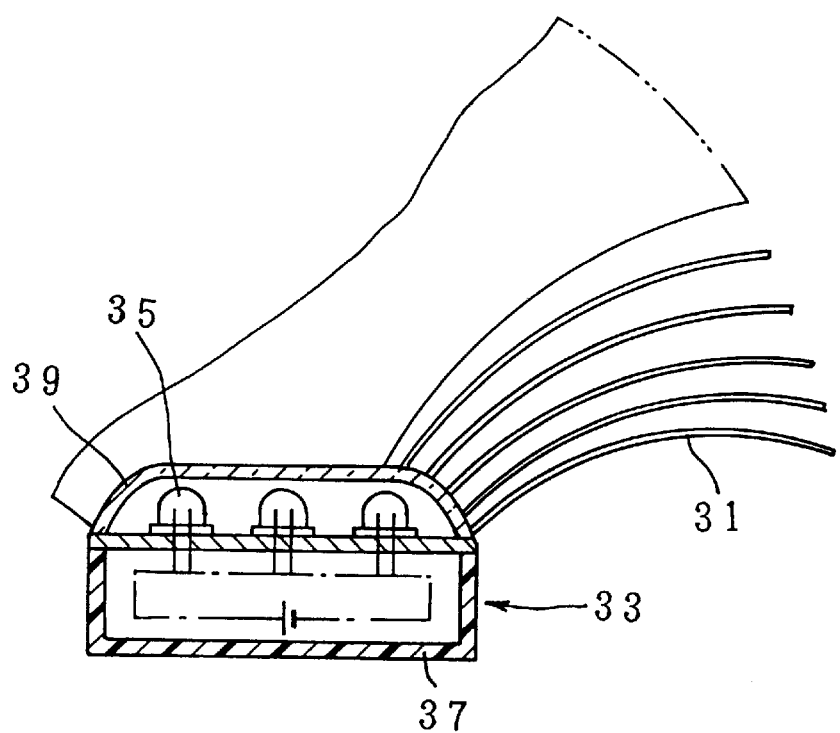
FIG. 3 is an overall view for illustrating construction of a photo-decoration according to a Second Preferred Embodiment of the present photo-catalyzer which is partly depicted in cross-section.

FIG. 3 illustrates a Second Preferred Embodiment of the present photo-catalyzer. This photo-catalyzer is constructed as a decoration. FIG. 3 illustrates the decoration partly in a cross-section. This decoration comprises a plurality of glass fibers 31, a base 33, and a plurality of light-emitting diodes 35 accommodated in the base 33.

The base 33 includes a box-shaped case 37, and a transparent upper member 39. The transparent upper member 39 constitutes a lid for the case 37. In the transparent upper member 39, all of the glass fibers 31 are buried at one of their opposite ends. A dry-cell battery is disposed under the light-emitting diodes 35.

Figure 4:
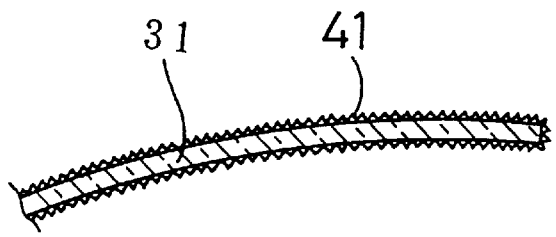
FIG. 4 is an enlarged partial cross-sectional view for illustrating a glass fiber of the Second Preferred Embodiment depicted in FIG. 3.

FIG. 4 illustrates one of the glass fibers 31 in an enlarged, partial cross-sectional view. As illustrated in FIG. 4, a titanium dioxide film 41, constituting a photo-catalyst, is disposed on the entire surface of the glass fiber 31. The titanium dioxide film 41 is vapor-deposited by a PVD process, and is semi-transparent pale yellow.

The light-emitting diodes 35 are small light-emitting devices, respectively, and comprise a tip and a molded lens. The tip includes a gallium nitride (GaN)-based photo-semiconductor crystal having a p-n junction and emitting light. The molded lens encloses the tip therein and gives the emitted light direction. The light-emitting diodes 35 emit light (or electromagnetic waves) having a wavelength from 360 to 400 nm, namely, they emit intense blue light together with ultraviolet light.

The intense blue light enters the glass fibers 31 through the transparent upper member 39, and travels the central portion of the glass fibers 31 to another of the opposite ends of the glass fibers 31. In the course of traveling, a portion of the blue light goes into the titanium dioxide film 41, and is released through the titanium dioxide film 41 to the outside. Accordingly, the glass fibers 31 glow a pale blue color to effect a decorative function. In addition, the ultraviolet light propagates similarly to the blue light, and a portion of the ultraviolet light enters the titanium dioxide film 41. Consequently, the titanium dioxide film 41 is activated to decompose organic substances, such as components of cigarette smoke, in ambient air. Thus, the decoration can also clean and purify the air.

Third Preferred Embodiment

Figure 5:
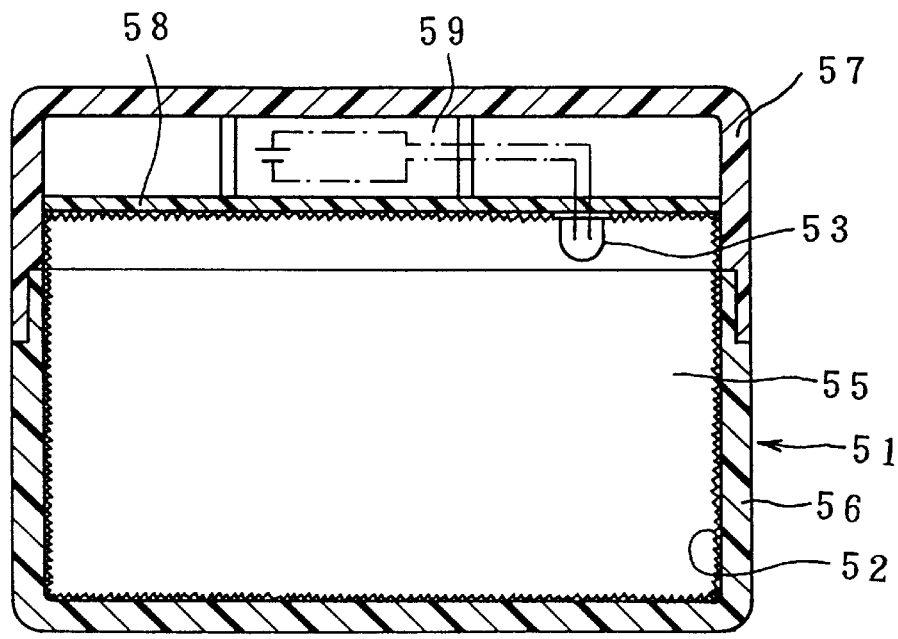
FIG. 5 is an overall cross-sectional view for illustrating a bacteria-repelling and deodorizing apparatus according to a Third Preferred Embodiment of the present photo-catalyzer.

FIG. 5 illustrates a Third Preferred Embodiment of the present photo-catalyzer, a bacteria-repelling and deodorizing box. This bacteria-repelling and deodorizing box comprises a housing 51, a titanium dioxide film 52, and a light-emitting diode 53. The housing 51 forms an accommodation chamber 55 therein. The titanium dioxide film 52 is disposed on all inner surfaces defining the accommodation chamber 55.

The housing 51 includes a box member 56 and a lid member 57. The box member 56 is formed of a synthetic resin and has an opening at the top. The lid member 57 is formed of a synthetic resin, and is held to the box member 56 so as to freely open and close over the opening of the box member 56. The lid member 57 is provided with a separator plate 58 so as to form a battery chamber 59 between its top portion and the separator plate 58. The battery chamber 59 accommodates a dry-cell battery therein.

The titanium dioxide film 52 is applied by coating an inorganic paint on the inner surfaces of the housing 51. The inorganic paint includes a titanium dioxide colloid as a pigment. Note that, contrary to ordinary pigments, the titanium dioxide colloid does not have an inert film on the titanium dioxide surface, but the titanium dioxide surface per se is exposed directly to light.

The light-emitting diode 53 is fastened to the separator plate 58 so as to irradiate the accommodation chamber 55. Moreover, the lid member 57 is provided with a switch (not shown) for turning on and off electric current to be supplied to the light-emitting diode 53.

The light-emitting diode 53 is a small light-emitting device, and comprise a tip and a molded lens. The tip includes a gallium nitride (GaN)-based photo-semiconductor crystal having a p-n junction and emitting light. The molded lens encloses the tip therein and gives the emitted light direction. The light-emitting diode 53 emits light (or electromagnetic waves) having a wavelength from 360 to 400 nm, namely, it emits ultraviolet light.

The bacteria-repelling and deodorizing box of the Third Preferred Embodiment accommodates a dry-cell battery in the battery chamber 59. When the switch is turned on, the light-emitting diode 53 produces ultraviolet light having a wavelength from 360 to 400 nm. This ultraviolet light travels in the accommodation chamber 55 to irradiate the titanium dioxide film 52 which is disposed on the inner surfaces defining the accommodation chamber 55. The ultraviolet light produces an oxidizing reactive surface on the titanium dioxide film 52. The oxidizing reactive surface decomposes odor components and repels bacteria present in the accommodation chamber 55. Thus, it is possible to always keep the accommodation chamber 55 clean and to use it comfortably.

Note that it is possible to use the bacteria-repelling and deodorizing box of the Third Preferred Embodiment as a medicine container or a cooler box.

Fourth Preferred Embodiment

Figure 6:
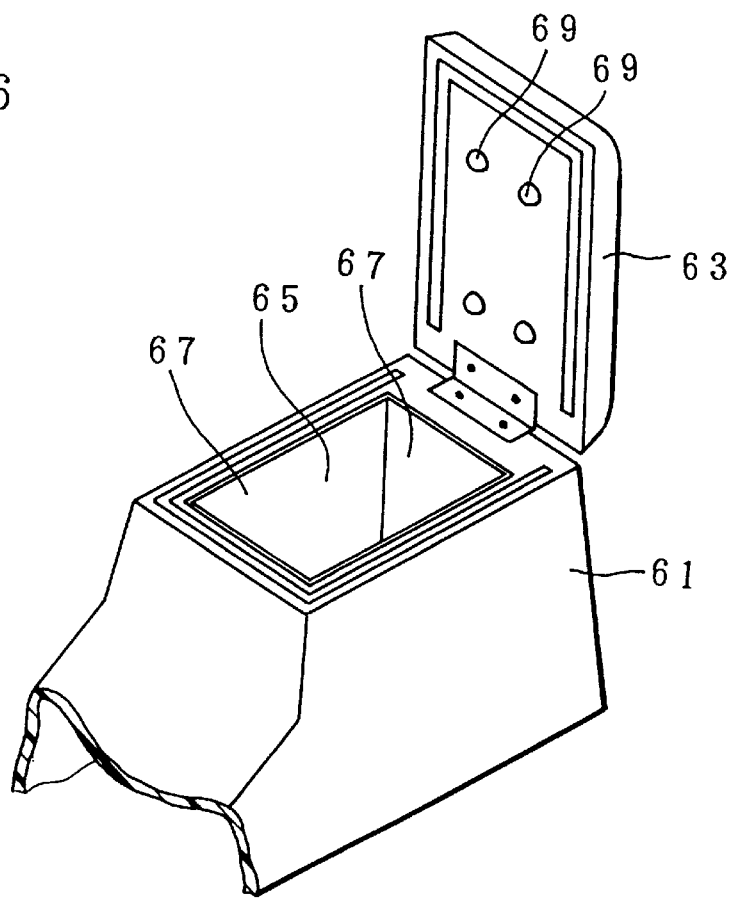
FIG. 6 is an overall perspective view for illustrating a console box capable of repelling bacteria and deodorizing according to a Fourth Preferred Embodiment of the present photo-catalyzer, the lid of the console box is opened.

FIG. 6 illustrates a Fourth Preferred Embodiment of the present photo-catalyzer, a console box capable of repelling bacteria, and deodorizing. As illustrated in FIG. 6, this console box comprises a body 61, and a lid member 63. The body 61 is installed in a central location in a passenger compartment of automobiles. The lid member 63 is hingeably attached to the body 61.

The body 61 is provided with an accommodation chamber 65 which has an opening at the top. On the inner wall surfaces defining the accommodation chamber 65, there is disposed a titanium dioxide film 67. The titanium dioxide film 67 is applied by coating an inorganic paint on the inner wall surfaces. The inorganic paint includes a titanium dioxide colloid as a pigment.

The light-emitting diodes 69 are fastened to the inside of the lid member 63 so as to shine ultraviolet light into the accommodation chamber 65. The light-emitting diodes 69 are small light-emitting devices, respectively, and comprise a tip and a molded lens. The tip includes a gallium nitride (GaN)-based photo-semiconductor crystal having a p-n junction and emitting light. The molded lens encloses the tip therein and gives the emitted light direction. The light-emitting diodes 69 produce light (or electromagnetic waves) having a wavelength from 360 to 400 nm.

When an automotive battery (not shown) supplies electric current to the light-emitting diodes 69 disposed in the lid member 63, the light-emitting diodes 69 irradiate ultraviolet light having a wavelength from 360 to 400 nm onto the titanium dioxide film 67 which is disposed on the inner wall surfaces defining the accommodation chamber 65. The ultraviolet light activates the titanium dioxide film 67, and provides an oxidizing reactive surface on the titanium dioxide film 67. The oxidizing reactive surface destroys or repels bacteria, and decomposes odor components present in the accommodation chamber 65. Thus, it is possible to always keep the accommodation chamber 65 clean and to use it comfortably.

Fifth Preferred Embodiment

Figure 7:
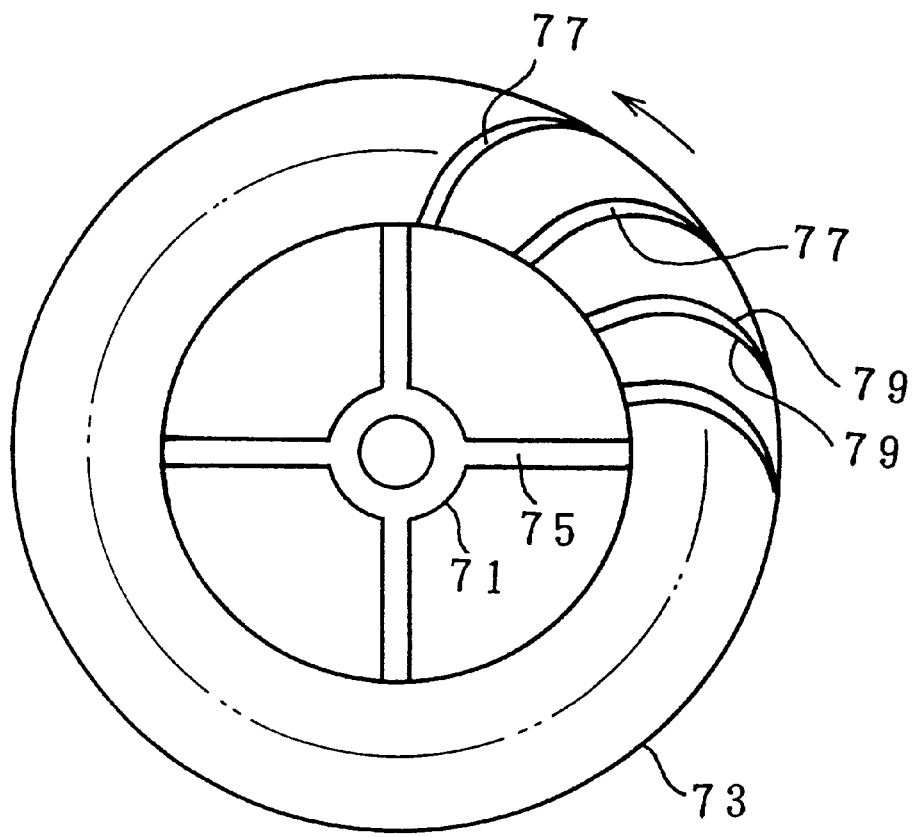
FIG. 7 is an abbreviated partial plan view for illustrating a fan capable of purifying air according to a Fifth Preferred Embodiment of the present photo-catalyzer.

FIG. 7 illustrates a Fifth Preferred Embodiment of the present photo-catalyzer, a fan capable of purifying air. This fan is a so-called sirocco-type fan. As illustrated in FIG. 7, the fan is injection-molded integrally, and comprises a rotary shaft member 71, a ring-shaped side plate 73, four support pillars 75, and a plurality of blades 77. The support pillars 75 connect the rotary shaft member 71 with the side plate 73. The blades 77 extend from the side plate 73 in the axial direction, and are disposed apart from each other at predetermined intervals. In FIG. 7, some of the blades 77 are omitted.

Over the entire surface of the blades 77, there is disposed a titanium dioxide film. The titanium dioxide film 79 is applied by coating an inorganic paint on the entire surface of the blades 77. The inorganic paint includes a titanium dioxide colloid as a pigment. Note that, contrary to ordinary pigments, the titanium dioxide colloid does not have an inert film on the titanium dioxide surface, but the titanium dioxide surface per se is exposed directly to light.

The fan rotates in the counter-clockwise direction as illustrated by the arrow of FIG. 7 to transfer air from the center in a radial direction.

In the fan capable of purifying air of the Fifth Preferred Embodiment, when the blades 77 are irradiated with ultraviolet light, the titanium dioxide film 79 is activated to provide an oxidizing reactive surface. The reactive surface efficiently purifies air which contacts the blades 77. In particular, air is driven from the center of the fan to the periphery in a radial direction as the blades rotate, and air flows along the surface of the blades 77. Thus, a large amount of air contacts the titanium dioxide film 79 which is disposed on the surface of the blades 77. As a result, the fan can efficiently clean and purify a large amount of air.

Sixth Preferred Embodiment

Figure 8:
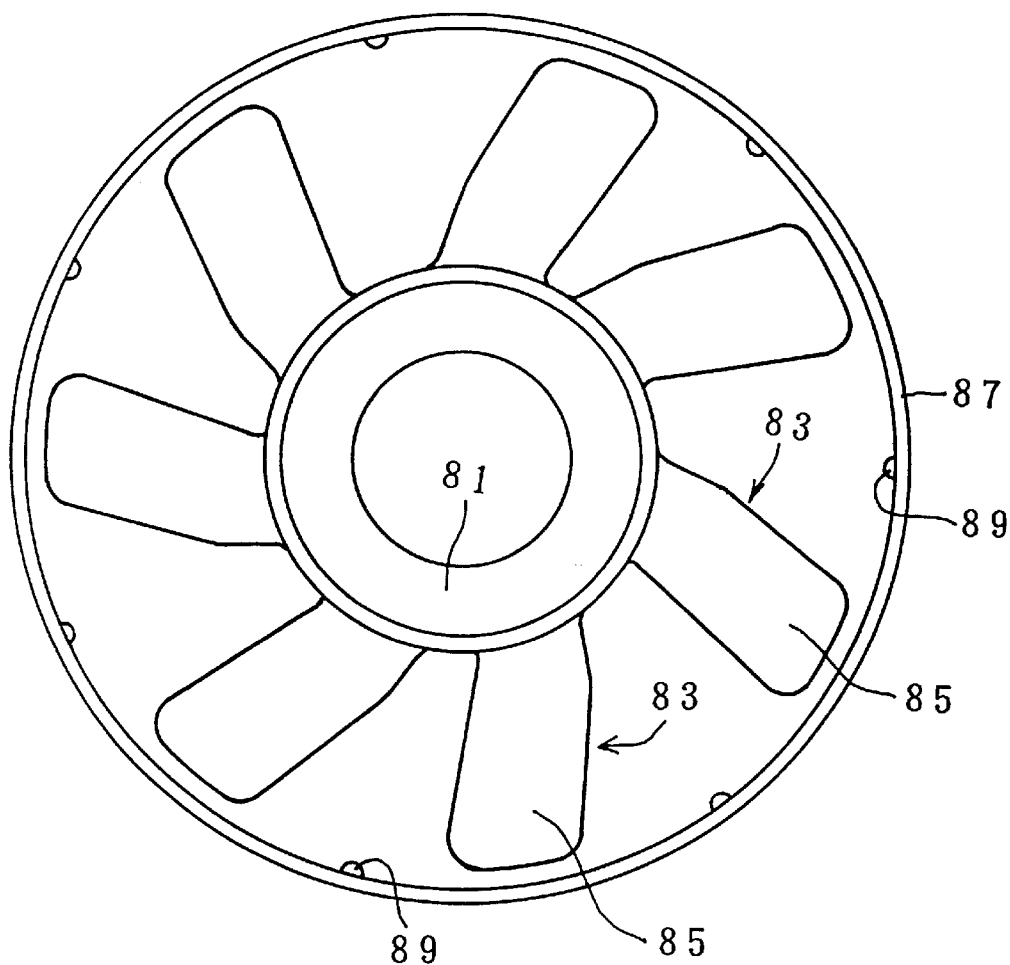
FIG. 8 is a plan view for illustrating a fan capable of purifying air according to a Sixth Preferred Embodiment of the present photo-catalyzer.

FIG. 8 illustrates a Sixth Preferred Embodiment of the present photo-catalyzer, a fan capable of purifying air. This fan is an ordinary propeller-type fan. As illustrated in FIG. 8, the fan comprises a rotary shaft member 81, a plurality of blades 83, a titanium dioxide film 85, a cylindrically-shaped guide member 87, and a plurality of light-emitting diodes 89. The blades 83 extend radially from the rotary shaft member 81 and are disposed apart from each other at predetermined intervals. The titanium dioxide film 85 is disposed on the entire surface of the blades 83. The guide member 87 is disposed so as to surround the blades 83. The light-emitting diodes 89 are disposed on the inner peripheral surface of the guide member 87 and are spaced at equal intervals. The titanium dioxide film 85 is applied by coating an inorganic paint on the entire surface of the blades 83. The inorganic paint includes a titanium dioxide colloid as a pigment.

The light-emitting diodes 89 are small light-emitting devices, respectively, and comprise a tip and a molded lens. The tip includes a gallium nitride (GaN)-based photo-semiconductor crystal having a p-n junction and emitting light. The molded lens encloses the tip therein and gives the emitted light direction. The light-emitting diodes 89 produce light (or electromagnetic waves) having a wavelength from 360 to 400 nm, namely, they emit ultraviolet light.

In service, the fan capable of purifying air of the Sixth Preferred Embodiment is fastened to a driving shaft of a driving motor. When the driving motor is actuated, an electric current is supplied to the light-emitting diodes 89 simultaneously. The light-emitting diodes 89 produce ultraviolet light. The blades 83 rotate as the driving motor rotates, and push and drive air in the axial direction.

The ultraviolet light produced by the light-emitting diodes 89 irradiates the titanium dioxide film 85 which is disposed on the surface of the blades 83, and activates the surface of the titanium dioxide film 85. The activated surface operates as a photo-catalyst, and efficiently decomposes odor components, and components of cigarette smoke, in the air. Thus, the fan purifies air. In particular, the fan can purify a large amount of time in a unit time, because the surface of the blades 83 contacts fresh air continuously.

The fan capable of cleaning and purifying air of the Sixth Preferred Embodiment can be incorporated into a variety of apparatuses as an air blower, because it is provided with a photo-catalyst as well as an ultraviolet source.

Seventh Preferred Embodiment

Figure 9:
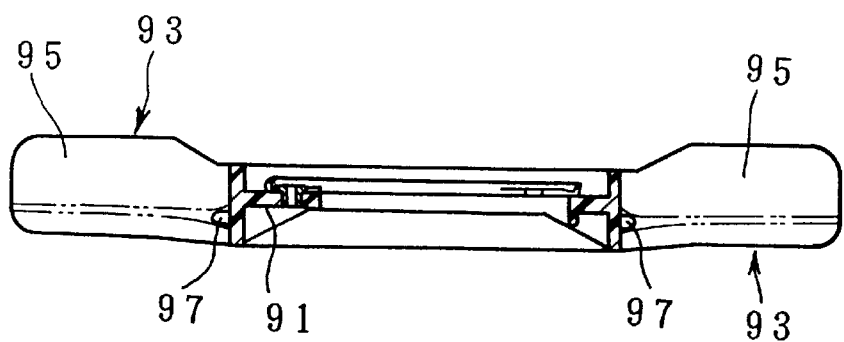
FIG. 9 is a transverse cross-sectional view for illustrating a fan capable of purifying air according to a Seventh Preferred Embodiment of the present photo-catalyzer.

FIG. 9 illustrates a Seventh Preferred Embodiment of the present photo-catalyzer, a fan capable of purifying air. This fan is an ordinary propeller-type fan. As illustrated in FIG. 9, the fan comprises a rotary shaft member 91, a plurality of blades 93, a titanium dioxide film 95, and a plurality of light-emitting diodes 97. The blades 93 extend radially from the rotary shaft member 91 and are disposed apart from each other at predetermined intervals. The titanium dioxide film 95 is disposed on the entire surface of the blades 93. The light-emitting diodes 97 are buried in the boundary between the rotary shaft member 91 and the blades 93. Note that the rotary shaft member 91 and the blades 93 are injection-molded integrally with a transparent resin which transmits ultraviolet light. After the injection molding, the light-emitting diodes 97 are buried in the rotary shaft member 91 adjacent to the blades 93.

The titanium dioxide film 95 is vapor-deposited on the entire surface of the blades 93 by a PVD process, and is semi-transparent pale yellow.

In the fan capable of purifying air of the Seventh Preferred Embodiment, the blades 93 are utilized as a photo-conductor, that is, the ultraviolet light produced by the light-emitting diodes 97 is transmitted to the surface of the blades 93 through the inside of the blades 93. At the surface of the blades 93, the ultraviolet light irradiates the titanium dioxide film 95 to activate the titanium dioxide film 95. The blades 93 send out air, and accordingly contact a large amount of fresh air at all times. Thus, a large amount of air is brought into contact with the titanium dioxide film 95 disposed on the blades 93, and thereby organic substances, such as odor components and components of cigarette smoke, in the air are decomposed and removed. Therefore, the fan can efficiently clean and purify air.

Eighth Preferred Embodiment

Figure 10:
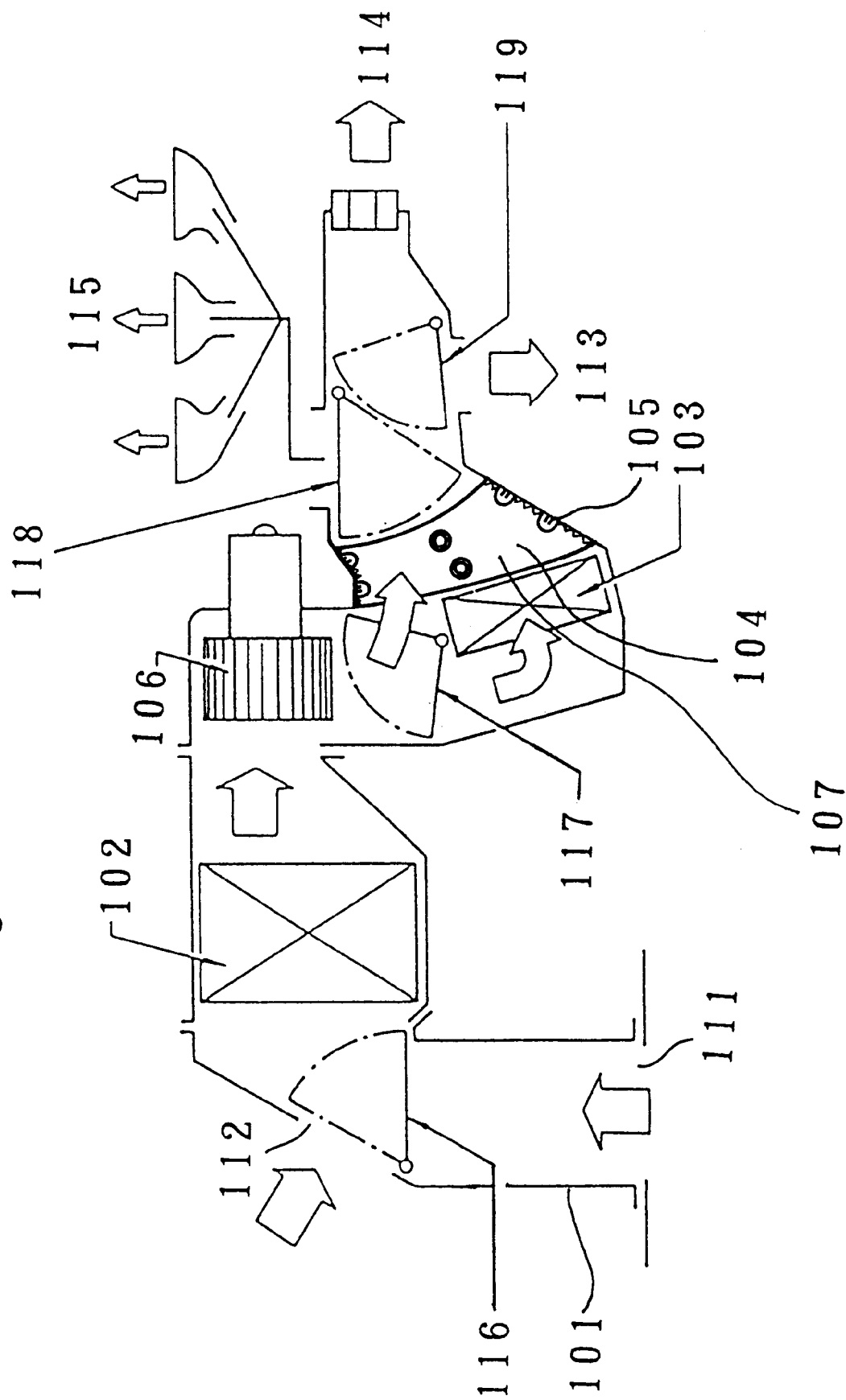
FIG. 10 is a cross-sectional view for illustrating major portions of an air conditioner capable of purifying air according to an Eighth Preferred Embodiment of the present photo-catalyzer.

FIG. 10 illustrates a cross-sectional view of major portions of an Eighth Preferred Embodiment of the present photo-catalyzer, an air conditioner capable of purifying air. This air conditioner is for automobiles, and comprises a duct 101, an evaporator 102, a heater core 103, a titanium dioxide film 104, a plurality of light-emitting diodes 105, and a blower 106. The evaporator 102 constitutes a cooler.

The duct 101 is provide with an external-air inlet port 111, an internal-air inlet port 112, a heated-air outlet port 113, a cooled-air outlet port 114, and a defrosted-air outlet port 115. The duct 101 is constructed by connecting a plurality of duct units. The duct 101 is further provided with an external-air-and-internal-air switching damper 116, an air-mixing damper 117, a defroster damper 118, and a heater-and-cooler switching damper 119. The heater-and-cooler switching damper 119 switches the heated-air outlet port 113 and the cooled-air outlet port 114.

The evaporator 102 vaporizes a liquid coolant which is supplied from a compression refrigerator (not shown), and cools air by the heat of vaporization. The evaporator 102 is integrally constructed with a heat exchanger (not shown).

The heater core 103 heats air with hot water used to cool an engine, and is integrally constructed with a heat exchanger (not shown).

Figure 11:
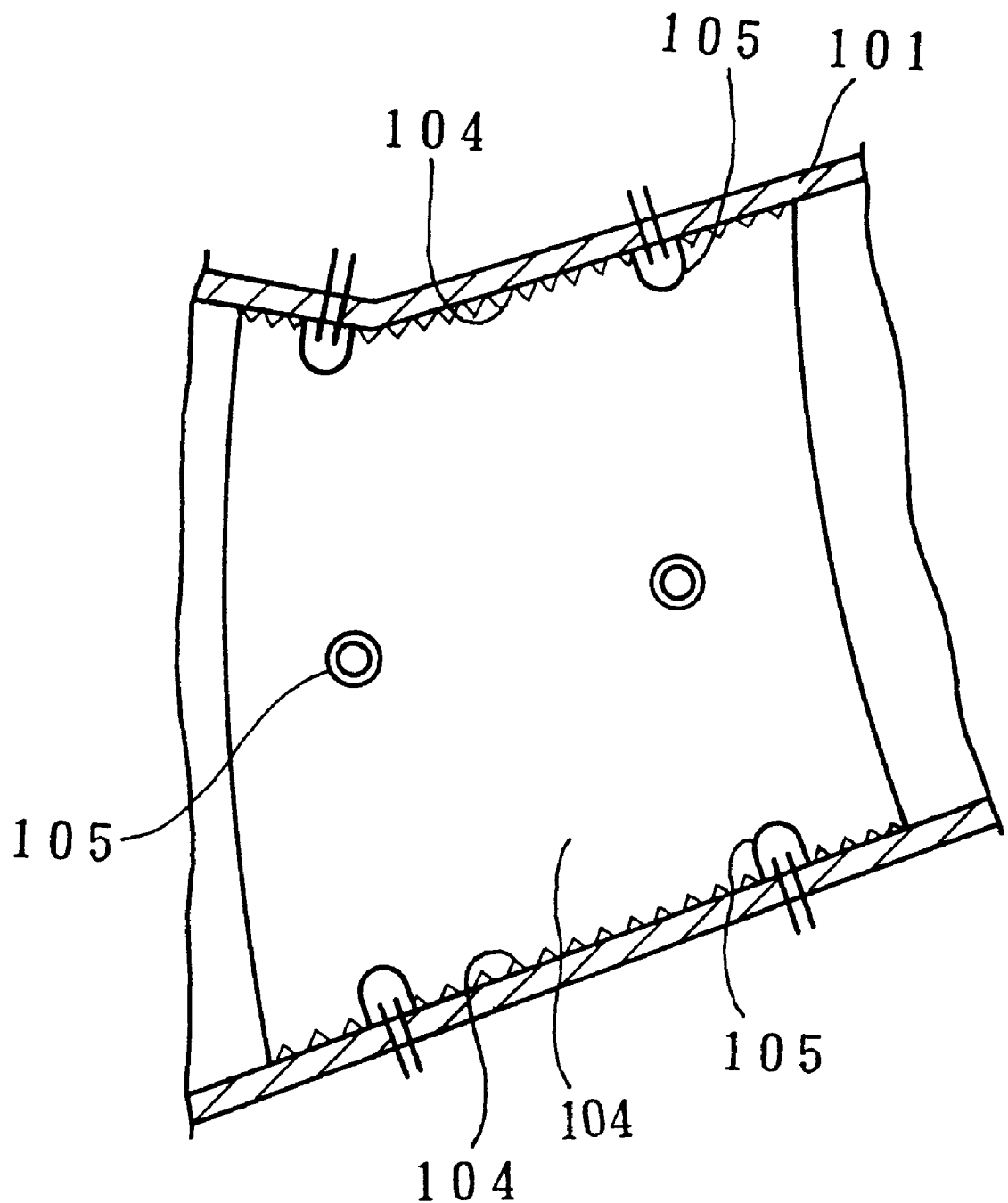
FIG. 11 is an enlarged cross-sectional view for illustrating an air purifying apparatus in the air conditioner depicted in FIG. 10.

The titanium dioxide film 104 and the light-emitting diodes 105 constitute an air purifier 107. FIG. 11 illustrates an enlarged cross-sectional view of the air purifier 107. The titanium dioxide film 104 is disposed on the inner wall of the duct 101 on the immediate upstream side with respect to the outlet ports 113–115, and on the downstream side with respect to the heater core 103 and the blower 106. The titanium dioxide film 104 is applied so as to go around the inner wall of the duct 101. The titanium dioxide film 104 is applied by coating an inorganic paint on the inner wall of the duct 101. The inorganic paint includes a titanium dioxide colloid as a pigment. Note that, contrary to ordinary pigments, the titanium dioxide colloid does not have an inert film on the titanium dioxide surface, but the titanium dioxide surface per se is exposed directly to light.

As illustrated in FIG. 11, the light-emitting diodes 105 are disposed in two rows in the duct 101 where the titanium dioxide film 104 is disposed. The light-emitting diodes 105 are positioned in the interior of the duct 101 substantially in the central region thereof, and are spaced at equal intervals around the inner surface thereof.

The light-emitting diodes 105 are small light-emitting devices, respectively, and comprise a tip and a molded lens. The tip includes a gallium nitride (GaN)-based photo-semiconductor crystal having a p-n junction and emitting light. The molded lens encloses the tip therein and gives the emitted light direction. The light-emitting diodes 105 produce light (or electromagnetic waves) having a wavelength from 360 to 400 nm, namely, they emit ultraviolet light.

The operations of the thus constructed air conditioner capable of purifying air of the Eighth Preferred Embodiment are hereinafter described. The blower 106 is rotated to push air through the duct 101, and the external-air inlet port 111 or the internal-air inlet port 112 delivers air into the duct 101. The air introduced into the duct 101 is cooled or heated by the evaporator 102 or the heater core 103, respectively, or is cooled and heated thereafter by the evaporator 102 and the heater core 103. Thus, the air is conditioned to a desired temperature and humidity, and transferred to the air purifier 107.

In the air purifier 107, the light-emitting diodes 105 emit ultraviolet light to irradiate the titanium dioxide film 104. Being subjected to the ultraviolet irradiation, the titanium dioxide film 104 is activated to exhibit a strong oxidizing action. The air introduced into the duct 101 and delivered therethrough contacts the titanium dioxide film 104, and thereby odor components and smoke components in the air are oxidized and decomposed. In the air purifier 107, the air is conditioned to a desired temperature and humidity, and is thus purified. Eventually, the purified air, conditioned to a desired temperature and humidity, is blown into an occupation compartment out of the heated-air outlet port 113, the cooled-air outlet port 114, or the defrosted-air outlet port 115.

Note that, instead of the air purifier 107 employed in the Eighth Preferred Embodiment, a titanium dioxide film can be disposed on the surface of the fins of the blower 106, and such a titanium dioxide film can be irradiated by ultraviolet light which is emitted from a light-emitting diode. Moreover, an independent air purifier can be constructed by incorporating a titanium dioxide film and a light-emitting diode for irradiating ultraviolet light onto the titanium dioxide therein, and such an independent air purifier can be disposed in the duct 101.

Ninth Preferred Embodiment

Figure 12:
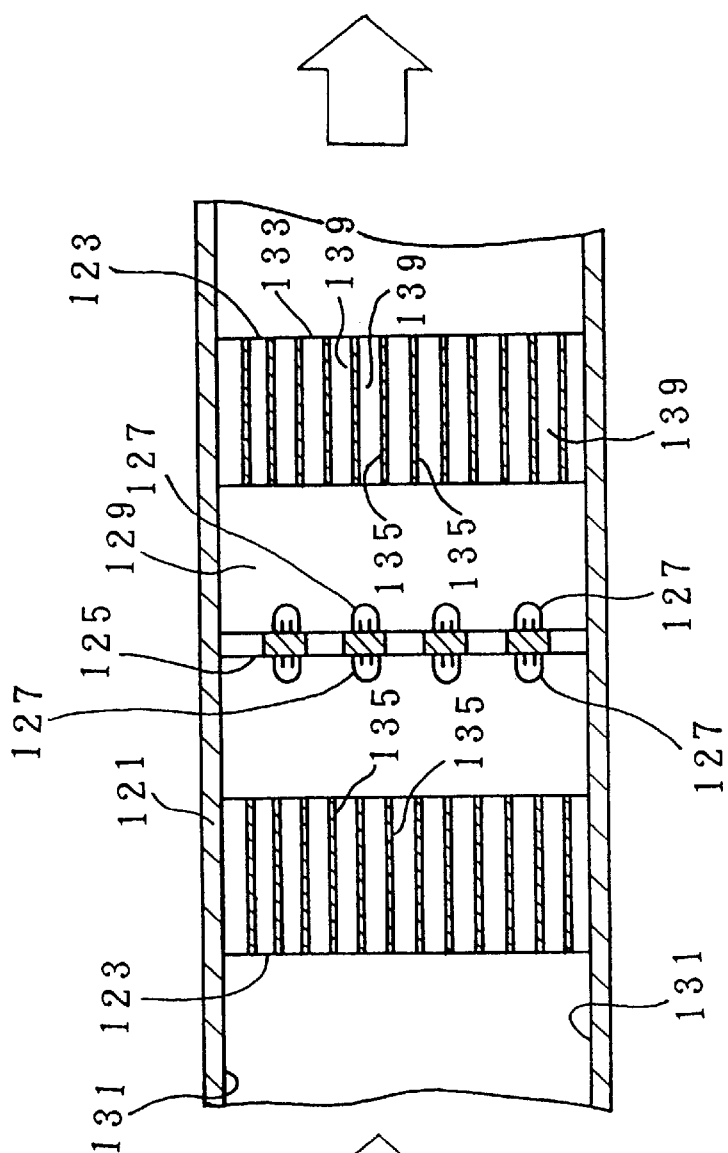
FIG. 12 is a cross-sectional view for illustrating an air purifying apparatus according to a Ninth Preferred Embodiment of the present photo-catalyzer.

FIG. 12 illustrates a Ninth Preferred Embodiment of the present photo-catalyzer, an air purifier. This air purifier comprises a metallic tubular case 121, two honeycomb-shaped-support catalysts 123, a perforated plate 125, and a plurality of light-emitting diodes 127. The honeycomb-shaped-support catalysts 123 are disposed in a tubular bore 129 of the case 121, are spaced by an interval therein, and are fastened to an inner wall 131 thereof. The perforated plate 125 is disposed at an intermediate position between the two honeycomb-shaped-support catalysts 123, and is fastened to an inner wall of the case 121. The light-emitting diodes 127 are fastened to opposite surfaces of the perforated plate 125.

Figure 13:
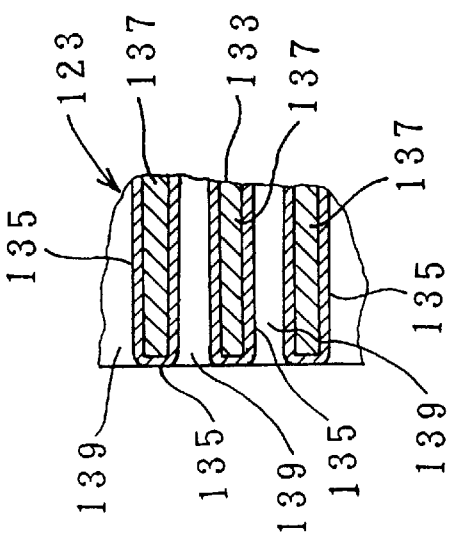
FIG. 13 is an enlarged partial cross-sectional view for illustrating a honeycomb-shaped support in the air purifying apparatus depicted in FIG. 12.

FIG. 13 is an enlarged partial cross-sectional view of the honeycomb-shaped-support catalysts 123. As illustrated in FIG. 13, the honeycomb-shaped-support catalysts 123 include a honeycomb-shaped support 133 made of a ceramic compound, and a titanium dioxide film 135. The titanium dioxide film 135 is disposed on end surfaces and wall surfaces of cellular walls 137 of the honeycomb-shaped support 133. The honeycomb-shaped-support catalysts 123 are provided with a plurality of through bores 139 which penetrate therethrough and are parallel to each other.

The titanium dioxide film 135 is formed in the following manner: a colloidal fine powder of titanium dioxide and a binder of water glass (i.e., sodium silicate) are mixed, and the mixture is dispersed in water to prepare a slurry. Then, a honeycomb-shaped support is immersed into the resulting slurry, and is thereafter taken out of the slurry to dry. Note that, contrary to ordinary pigments, the titanium dioxide colloid does not have an inert film on the titanium dioxide surface, but the titanium dioxide surface per se is exposed directly to light.

The perforated plate 125 is formed on the whole as a disk, and is provided with a plurality of holes. The holes have a relatively large inside diameter, and are disposed so as to form a grille-like pattern. The light-emitting diodes 127 are fastened at a central portion of the grille-like pattern on both of the opposite surfaces of the perforated plate 125.

The light-emitting diodes 127 are small light-emitting devices, respectively, and comprise a tip and a molded lens. The tip includes a gallium nitride (GaN)-based photo-semiconductor crystal having a p-n junction and emitting light. The molded lens encloses the tip therein, and gives the emitted light direction. The light-emitting diodes 127 produce light (or electromagnetic waves) having a wavelength from 360 to 400 nm, namely, they emit ultraviolet light.

In the air purifier of the Ninth Preferred Embodiment, air to be purified is delivered in the direction specified by the arrows of FIG. 12, namely, the air is transferred from the left-hand side of the tubular bore 129 to the right-hand side thereof in the drawing. Specifically, the air is passed through the through bores 139 of the left-hand-side honeycomb-shaped-support catalyst 123, then passed through the perforated plate 125, and finally passed through the through bores 139 of the right-hand-side honeycomb-shaped-support catalyst 123.

When the light-emitting diodes 127 fastened to the perforated plate 125 are turned on, they produce ultraviolet light. The ultraviolet light irradiates the titanium dioxide film 135 disposed on the end surface of the honeycomb-shaped-support catalysts 123. The ultraviolet light then enters the through bores 139, and irradiates the titanium dioxide film 135 disposed on the surface of the cellular walls of the through bores 139. When the titanium dioxide film 135 is irradiated by ultraviolet light, it is activated to effect a strong oxidizing action. As a result, when organic substances in the air contact the activated titanium dioxide film 135 disposed on the end surface and the cellular wall surfaces of the honeycomb-shaped-support catalysts 123, they are oxidized and decomposed. Thus, the air purifier of the Ninth Preferred Embodiment cleans and purifies the air by oxidizing and decomposing odor components and smoke components in the air.

In the air purifier of the Ninth Preferred Embodiment, the titanium dioxide film 135 is disposed on all surfaces of the honeycomb-shaped supports 133. Consequently, the titanium dioxide film 135 occupies a large surface area with respect to the volume occupied by the honeycomb-shaped supports 133. Thus, the honeycomb-shaped-support catalysts 123 are downsized to a compact structure. Moreover, the air can pass through a plurality of the through bores 139 of the honeycomb-shaped supports 133 with a minimum of pressure loss.

In addition, since the light-emitting diodes 127 are extremely small, only a small space is required for incorporating them into the case 121. Accordingly, the air purifier of the Ninth Preferred Embodiment has a compact structure.

Tenth Preferred Embodiment

Figure 14:
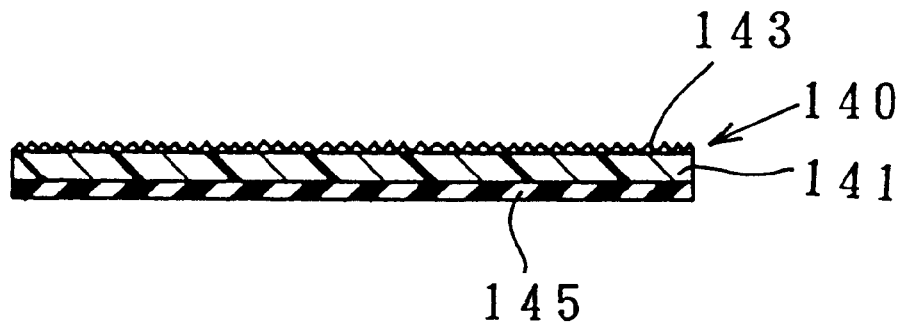
FIG. 14 is a cross-sectional view for illustrating a bacteria-repelling and deodorizing sheet according to a Tenth Preferred Embodiment of the present photo-catalyzer.

FIG. 14 illustrates a Tenth Preferred Embodiment of the present photo-catalyzer, a bacteria-repelling and deodorizing sheet, in cross-section. This bacteria-repelling and deodorizing sheet comprises a base layer 141, a top layer 143, and a sticky layer 145. The base layer 141 is formed by extrusion-molding a fluorocarbon resin in a film shape. The top layer 143 is formed in the following manner: a titanium dioxide powder is mixed with a fluorocarbon resin emulsion and the resulting mixture is coated and dried on one of the opposite surfaces of the base layer 141. The sticky layer 145 is disposed on another one of the opposite surfaces of the base layer 141, and includes an unvulcanized rubber. Note that the base layer 141 and the top layer 143 constitutes a sheet 140.

The bacteria-repelling and deodorizing sheet has a bacteria-repelling and destroying function by means of the photo-catalytic action resulting from the titanium dioxide included in the top layer 143. Moreover, it exhibits a high mechanical strength because it is provided with the base layer 141. It is less likely to break, and accordingly it is useful in service.

Eleventh Preferred Embodiment

Figure 15:
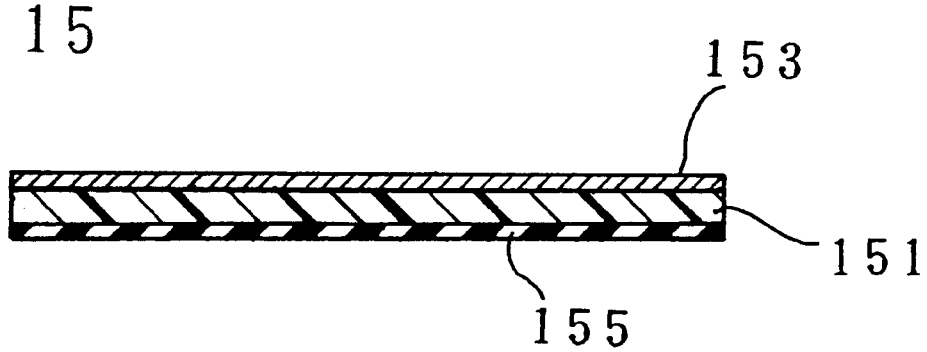
FIG. 15 is a cross-sectional view for illustrating a bacteria-repelling and deodorizing sheet according to an Eleventh Preferred Embodiment of the present photo-catalyzer.

FIG. 15 illustrates an Eleventh Preferred Embodiment of the present photo-catalyzer, a bacteria-repelling and deodorizing sheet, in cross-section. This bacteria-repelling and deodorizing sheet comprises a base layer 151, a titanium dioxide film 153, and a sticky layer 155. The base layer 151 is formed by extrusion-molding a fluorocarbon resin in a film shape. The titanium dioxide film 153 is vapor-deposited on one of the opposite surfaces of the base layer 151 by a physical vapor deposition process. The sticky layer 155 is disposed on another one of the opposite surfaces of the base layer 151, and includes an unvulcanized rubber.

The bacteria-repelling and deodorizing sheet has a bacteria-repelling and destroying function by means of the photo-catalytic action resulting from the titanium dioxide film 153. Moreover, the titanium dioxide film 153 is provided with a beautiful surface which is fully glossy, because it is a vapor-deposited film. Thus, the sheet produces a decorative effect as well.

Twelfth Preferred Embodiment

Figure 16:
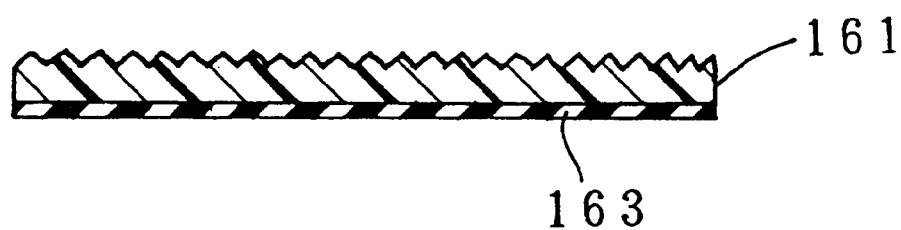
FIG. 16 is a cross-sectional view for illustrating a bacteria-repelling and deodorizing sheet according to a Twelfth Preferred Embodiment of the present photo-catalyzer.

FIG. 16 illustrates a Twelfth Preferred Embodiment of the present photo-catalyzer, a bacteria-repelling and deodorizing sheet, in cross-section. This bacteria-repelling and deodorizing sheet comprises a sheet 161 and a sticky layer 163. The sheet 161 is molded out of a mixture which includes a fluorocarbon resin emulsion and a titanium dioxide powder, and has a relatively heavy thickness (i.e., the sheet 161 can preferably have a thickness of 5 mm at the largest, and the sticky layer 163 can preferably have a thickness of 10 mm at the largest. The sticky layer 163 is disposed on one of the opposite surfaces of the sheet 161, and includes an unvulcanized rubber.

Concerning the mechanical strength of the sheet 161 per se, the bacteria-repelling and deodorizing sheet of the Twelth Preferred Embodiment is inferior to that of the Tenth Preferred Embodiment because there is no base layer. However, it has a remarkably high bacteria-repelling and deodorizing function equivalent to that of the Tenth Preferred Embodiment.

Thirteenth Preferred Embodiment

Figure 17:
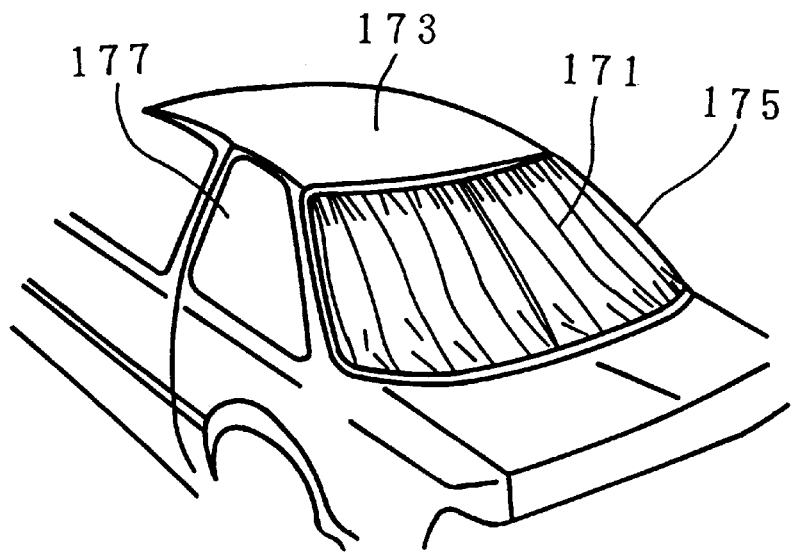
FIG. 17 is a perspective view for illustrating a vehicle curtain according to a Thirteenth Preferred Embodiment of the present photo-catalyzer, the vehicle curtain functions as a light shield for the vehicle.
Figure 18:
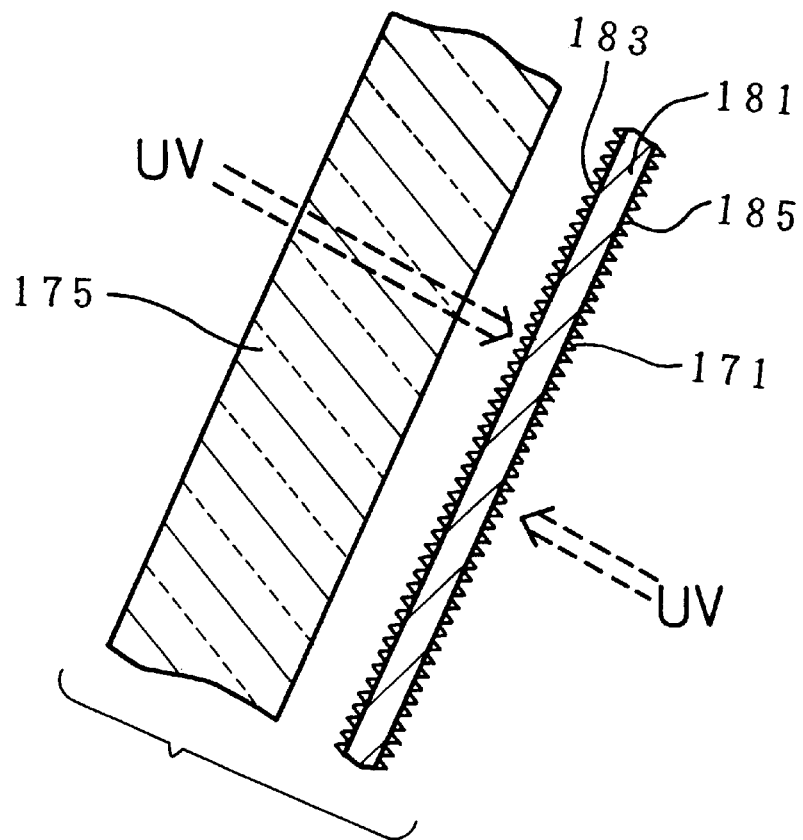
FIG. 18 is a cross-sectional view for illustrating a major portion of the vehicle curtain depicted in FIG. 17.

FIG. 17 illustrates a Thirteenth Preferred Embodiment of the present photo-catalyzer, a vehicle curtain which functions as a light shield for a vehicle. FIG. 18 is a cross-sectional view for illustrating the major portions of the vehicle curtain depicted in FIG. 17.

Similar to ordinary vehicle curtains, a vehicle curtain 171 according to the Thirteenth Preferred Embodiment can be disposed in an automobile 173 in an extended manner, namely, it can be disposed so as to face a rear windshield 175 or a side window 177 on a passenger compartment side, or it can be disposed between front and rear seats so as to shield a space (not shown) above the seats. As a whole, the vehicle curtain 171 shields at least some incident light. The incident light comes from the rear windshield 175 or side window 177 which faces the vehicle curtain 171. In FIG. 17, the vehicle curtain 171 is, for instance, disposed so as to face the inner surface of the rear windshield 175.

Specifically, as illustrated in FIG. 18, the vehicle curtain 171 comprises a substrate 181, and photo-catalysts 183 and 185. The substrate 181 includes a curtain cloth capable of shielding light. The photo-catalysts 183 and 185 include a titanium dioxide film which is disposed continuously in the plane of the substrate 181. The curtain cloth constituting the substrate 181 is made from a heat-resistant material, for example, a glass-fiber-woven cloth. When the photo-catalysts 183 and 185 are applied to the curtain cloth, the curtain cloth provides photo-catalyst-reactive surfaces which can come into contact with a medium to be processed (i.e., air in the Thirteenth Preferred Embodiment). As for specific heat-resistant curtain cloths like the glass-fiber-woven cloth, a variety of known heat-resistant cloths can be employed as far as they exhibit flexibility adequate for curtain cloths. Together with a light rainbow-like color exhibited by the photo-catalysts 183 and 185, the substrate 181 made from a glass-fiber-woven cloth is expected to provide the property of light-shielding as a whole to a completed vehicle curtain. However, as described later, the substrate 181 is not required to be perfectly light-shielding, namely, it can preferably allow light to be partially transmitted. For instance, the substrate 181 can permit ultraviolet light to pass through the externally-disposed photo-catalyst 183 and itself, and to reach the internally-disposed photo-catalyst 185. In other words, the term "light-shielding" means to shield the transmission of light at least partially.

For instance, the substrate 181 has opposite planar surfaces separated by a certain thickness. The photo-catalysts 183 and 185 are disposed on both of the opposite surfaces. Ultraviolet light (UV), such as sunlight, irradiates the photo-catalyst 183 disposed on the outside surface of the substrate 181 to activate the photo-catalyst 183. At least part of the ultraviolet light transmits through the externally-disposed photo-catalyst 183 and the substrate 181, and irradiates the photo-catalyst 185 disposed on the internal surface of the substrate 181 to activate the photo-catalyst 185 as well. The sunlight also falls on the other windows, such as the side window 177, and reaches the passenger compartment. The ultraviolet light component of this sunlight also irradiates the internally disposed photo-catalyst 185 to activate the photo-catalyst 185 as well.

In the vehicle curtain of the Thirteenth Preferred Embodiment, the titanium dioxide film constitutes the photo-catalysts 183 and 185, and titanium dioxide particles constitute the titanium dioxide film. It has been known that, when the particle diameter of the titanium dioxide particles is sufficiently small, the photo-catalysts 183 and 185 exhibit a high photo-catalytic action due to the "quantum size" effect, etc. Accordingly, it is preferred to form the titanium dioxide film as a transparent film in a thickness from 0.05 to 0.3 $\mu$m, more preferably from 0.1 to 0.2 $\mu$m, by a known sol-gel process. Moreover, it is preferred to laminate the thus formed films as a laminated film, for example, as a transparent film having a thickness of about 0.7 $\mu$m. Note that the term "transparent" herein includes semi-transparent, which exhibits the aforementioned pale rainbow-like colors.

The photo-catalysts 183 and 185 constituted by the titanium dioxide film can be, for instance, disposed by a sol-gel process on the opposite surfaces of the substrate 181 used as a support. In particular, the substrate 181 is prepared with a glass-fiber-woven cloth. A titanium dioxide colloid (or sol) is applied by a dip-coating process, a coating process or a spraying process on the opposite surfaces of the substrate 181, thereby forming a thin layer. The substrate 181 with the thin layer applied is heated gradually from room temperature to a predetermined temperature falling, for example, in a range from 600 to 700° C., thereby calcining the sol. Note that, in addition to the direct heating of the sol coated on the opposite surfaces of the substrate 181, it is possible to calcine the sol by gradually raising the temperature of the substrate 181 per se. If such is the case, it is possible to apply a titanium dioxide film, which is made from titanium dioxide particles having a sufficiently small particle diameter, on the opposite surfaces of the substrate 181. Moreover, such a titanium dioxide film can fasten tightly onto the substrate 181 which is made from glass fibers. In addition, such a titanium dioxide film has an anatase-type crystalline structure and makes a highly active photo-catalyst.

In addition to the sol-gel process described above, it is possible to employ a vapor-phase-growing process such as a vacuum deposition process or a chemical precipitation process, to deposit a highly active titanium dioxide film on the opposite surfaces of the substrate 181. For instance, a thin titanium-dioxide-film layer is applied on the opposite surfaces of the substrate 181 by a vapor-phase-growing process, such as a vacuum deposition process or a chemical precipitation process, and is calcined to form the photo-catalysts 183 and 185 including the titanium dioxide film. The calcination of the thin titanium-dioxide-film layer can be done in the following manner: the substrate 181 is heated to a predetermined temperature in advance, then a thin titanium-dioxide-film layer is deposited on the opposite surfaces of the heated substrate 181 by a vacuum deposition process, etc., and is calcined simultaneously. Alternatively, a thin titanium-dioxide-film layer can be deposited on the opposite surfaces of the substrate 181 by a vacuum deposition process, etc., and simultaneously the substrate 181 or the thin titanium-dioxide-film layer can be heated to a predetermined temperature. In addition, a thin titanium dioxide-film layer can be deposited on the opposite surfaces of the substrate 181 by a vacuum deposition process, etc., and thereafter the substrate 181 or the thin titanium dioxide-film layer can be heated to a predetermined temperature. Similar to the aforementioned sol-gel process, the photo-catalysts 183 and 185 are turned into an anatase-type crystalline structure by all of these calcination processes. Accordingly, the photo catalysts 183 and 185 are highly active and tightly fasten to the opposite surfaces of the substrate 181. In particular, in the Thirteenth Preferred Embodiment, the substrate 181 is comprised of a glass-fiber-woven cloth which can fully resist a high calcination temperature between 600 and 700° C. Thus, there is no danger of thermally affecting the substrate 181 during the formation of the highly active titanium dioxide film.

On the other hand, when a titanium dioxide film is disposed on the opposite surfaces of the substrate 181 by a process other than the above-described processes, for instance, when a titanium dioxide film is disposed on the opposite surfaces of the substrate 181 by a simple vacuum deposition process, a less active amorphous film is predominantly obtained in which brookite, anatasen and rutile structures coexist in extremely trace amounts.

The thus constructed vehicle curtain 171 of the Thirteenth Preferred Embodiment operates as hereinafter described.

In the vehicle curtain 171 of the Thirteenth Preferred Embodiment, the photo-catalysts 183 and 185 disposed on the opposite surfaces of the substrate 181 cause a photo-catalytic reaction in sunlight when irradiated by ultraviolet light having a wavelength from 360 to 400 nm. Sunlight is transmitted through the windshield 175 and ultraviolet light having a wavelength of around 400 nm irradiates the substrate 181 to activate the externally-loaded photo-catalyst 183. The ultraviolet light is transmitted through the substrate 181 and activates the internally-loaded photo-catalyst 185 because the substrate 181 is comprised of glass-fiber-woven cloth. Unless the ultraviolet light is completely absorbed by the photo-catalysts 183 and 185, the ultraviolet light will be transmitted through the substrate 181 over the entire vehicle curtain 171 and will activate the photo-catalysts 183 and 185 on the opposing side. At the same time, the ultraviolet component of sunlight is transmitted through the other window 177 to activate the internally-facing photo-catalyst 185, and transmits through the substrate 181 to activate the externally-facing photo-catalyst 183 as well. The thus activated photo-catalysts 183 and 185 decompose odor components in air by the photo-catalytic action, especially, by the oxidizing catalytic action, and thereby deodorize the air. The air in the passenger compartment can be circulated by an air conditioner (not shown) in the passenger compartment, thereby being dehumidified or further deodorized. As a result, it is possible to always keep the inside of the passenger compartment comfortable.

The photo-catalysts 183 and 185 effect their oxidizing catalytic activity not only to decompose odor components but also to oxidatively decompose organic components like cigarette tar, etc. Thus, the photo-catalyzers 183 and 185 disposed on the substrate 181 can decompose organic components. Further, the activated photo-catalyzers 183 and 185 have a sterilizing capability which results from the oxidizing catalytic action. Consequently, when the activated photo-catalyzers 183 and 185 contact micro-organisms, such as fungi, bacteria, or the like, in the air, the present invention can destroy or repel the micro-organisms. Hence, in addition to the deodorizing capability, the vehicle curtain 20 of the Thirteenth Preferred Embodiment has a capability of decomposing and removing cigarette-smoke components as well as a capability of destroying and repelling micro-organisms. Furthermore, the vehicle curtain 171 of the Thirteenth Preferred Embodiment can contact air over a surface area which is virtually equivalent to the surface area of the windshield 175, thereby providing a wide photo-catalytic reactive surface. Therefore, the vehicle curtain 171 of the Thirteenth Preferred Embodiment can deodorize or cleanse a large amount of air.

The substrate 181 comprises a glass-fiber-woven cloth. Glass fibers are unpleasant to the touch. However, the titanium dioxide-film photo-catalysts 183 and 185 are disposed on the opposite surfaces of the substrate 181, and accordingly they cover the surface of the cloth and cancel this unpleasant feeling.

The vehicle curtain 171 of the Thirteenth Preferred Embodiment naturally functions as a light shield for a vehicle in a manner similar to ordinary vehicle curtains.

In the thus constructed vehicle curtain 171 of the Thirteenth Preferred Embodiment, the photo-catalysts 183 and 185 oxidatively decompose organic components, such as odors and contaminants, in the passenger compartment, thereby cleaning and purifying the air in the passenger compartment. In addition, the photo-catalysts 183 and 185 purify and cleanse the substrate 181 itself, thereby keeping the substrate 181 clean. The vehicle curtain 171 per se has a variety of functions, such as the air-purifying function, and so on. As a result, when the vehicle curtain 171 is employed, it is possible to improve the passenger-compartment environment without employing conventional air purifiers and without providing a special space for carrying conventional air purifiers. In particular, the photo-catalysts 183 and 185 can be made highly active by calcining the titanium dioxide films, and closely attaching the photo-catalysts 183 and 185 onto the substrate 181 by calcination. Accordingly, the photo-catalysts 183 and 185 can carry out their variety of functions, like the air-purifying function, etc., more effectively.

Fourteenth Preferred Embodiment

Figure 19:
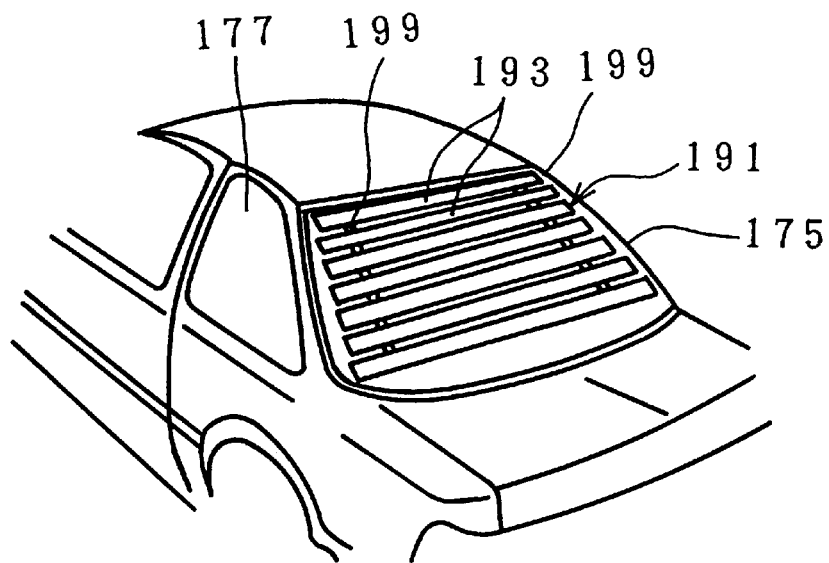
FIG. 19 is a perspective view for illustrating a vehicle blind according to a Fourteenth Preferred Embodiment of the present photo-catalyzer, the vehicle blind functions as a light shield for the vehicle.
Figure 20:
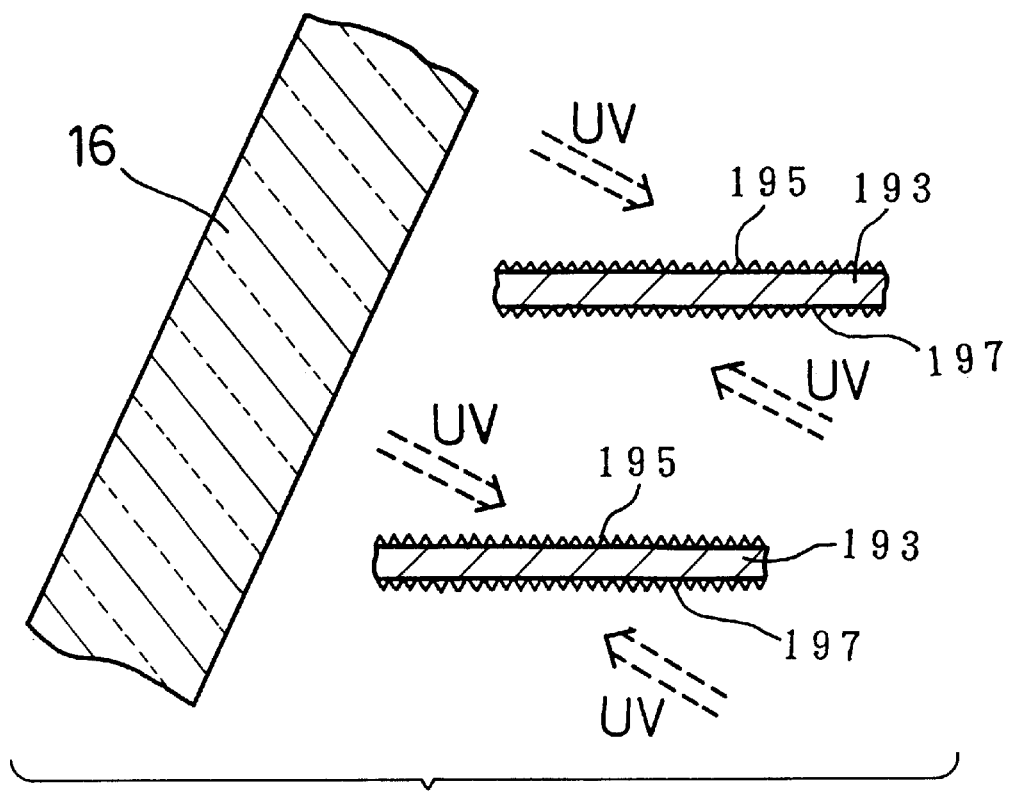
FIG. 20 is a cross-sectional view for illustrating a major portion of the vehicle blind depicted in FIG. 19.

A Fourteenth Preferred Embodiment of the present photo-catalyzer will be hereinafter described. In the description of the Fourteenth Preferred Embodiment, only the differences between the Fourteenth Preferred Embodiment and the Thirteenth Preferred Embodiment will be described in detail. In FIGS. 19 and 20, arrangements identical with those of the Thirteenth Preferred Embodiment are designated by the same reference numerals as those of the Thirteenth Preferred Embodiment, and will not be described.

FIG. 19 illustrates a Fourteenth Preferred Embodiment of the present photo-catalyzer, a vehicle blind which functions as a light shield for a vehicle. FIG. 20 is a cross-sectional view for illustrating the major portions of the vehicle curtain depicted in FIG. 19.

As illustrated in FIG. 19, a vehicle blind 191 of the Fourteenth Preferred Embodiment employs a plurality of slats 193 as a substrate. The slats 193 are disposed against the inner surface of a vehicle rear windshield 175, etc., and are provided with photo-catalysts 195 and 197 on the opposite surfaces. The photo-catalysts 195 and 197 are similar to those of the Thirteenth Preferred Embodiment, and are disposed on the opposite surfaces of the slats 193 in the same manner as the Thirteenth Preferred Embodiment. Except that the vehicle blind 191 of the Fourteenth Preferred Embodiment is provided with the photo-catalysts 195 and 197, it has the same arrangements as those of ordinary vehicle blinds, namely it includes a plurality of slats 193 constituting a substrate, and supporter members 199 for supporting the slats 193. The slats 193 are formed as elongated and uninterrupted members, are arranged parallel to each other with spaces between the slats, and are formed of a heat-resistant material. The supporter members 199 extend in the vertical direction, and hold the slats 193 at opposite ends of the slats 31 in the length-wise direction thereof. The supporter members 199 thus secure and give rigidity to the vehicle blind 191 as a whole. The slats 193 are usually formed of a known heat-resistant material, such as a metallic plate, etc. The slats 193 themselves are completely light shielding, but let sunlight enter into a passenger compartment through spaces between the slats. Alternatively, the slats 193 can be a plate-shaped rigid body having an uninterrupted long length and including a glass-fiber-woven cloth so that part of the sunlight can pass through the slats 193 per se.

In the vehicle blind 191 of the Fourteenth Preferred Embodiment, as illustrated in FIG. 19, the photo-catalysts 195 and 197 are disposed on the top and bottom surfaces of the substrate-constituting slats 193 in the same manner as the Thirteenth Preferred Embodiment, namely, titanium-dioxide-film layers are disposed continuously on the opposite surfaces of the slats 193, and are calcined. The process of applying the film, the film thickness, and the physical properties of the photo-catalysts 195 and 197 are identical with those of the photo-catalysts 183 and 185 of the Thirteenth Preferred Embodiment, and will not be described herein.

The operation of the thus constructed vehicle blind 191 of the Fourteenth Preferred Embodiment will be hereinafter described. Ultraviolet light (UV) in sunlight transmits through the rear windshield 175, and irradiates the slats 193 functioning as a substrate. Accordingly, the ultraviolet light activates the photo-catalysts 195 and 197 disposed on the top and bottom surfaces of the slats 193. The plurality of slats 193 constitute a substrate so that ultraviolet light is transmitted through the spaces between the slats 193. Therefore, the ultraviolet light shines on the photo-catalysts 195 and 197 substantially evenly by reflection between the top and bottom surfaces until it is eventually absorbed by the photo-catalysts 195 and 197. At the same time, ultraviolet light in sunlight enters through the other window 177, and reaches the passenger compartment to irradiate the slats 193 from the passenger-side of the vehicle blind. Hence, ultraviolet light irradiates the photo-catalysts 195 and 197 which are disposed on the top and bottom surfaces of the slats 193. Similar to the Thirteenth Preferred Embodiment, the thus activated photo-catalysts 195 and 197 decompose and deodorize the odor components in the air by their photo-catalytic action, especially by their oxidizing catalytic action, thereby purifying the air. Thus, the vehicle blind 191 keeps the passenger compartment comfortable. At the same time, the photo-catalyzers 195 and 197 not only decompose the organic components, like cigarette tar, in the air, but also destroys micro-organisms, such as the fungi or bacteria, etc., in the air. Hence, in addition to the deodorizing capability, the vehicle blind 191 of the Fourteenth Preferred Embodiment has the capability of decomposing and removing cigarette smoke components as well as the capability of destroying micro-organisms. Furthermore, in the vehicle blind 191 of the Fourteenth Preferred Embodiment, the slats 193 can contact air over a surface area which is virtually equivalent to the surface area of the windshield 175, thereby providing a wide photo-catalytic reactive surface. Therefore, the vehicle blind 191 of the Fourteenth Preferred Embodiment can deodorize or cleanse a large amount of air.

The vehicle blind 191 of the Fourteenth Preferred Embodiment naturally functions as a light shield for a vehicle in a manner similar to ordinary vehicle blinds.

In the thus constructed vehicle blind 191 of the Fourteenth Preferred Embodiment, the photo-catalysts 195 and 197 oxidatively decompose organic components, such as odors and contaminants, dispersed in the passenger compartment, thereby cleaning and purifying the air in the passenger compartment. In addition, the photo-catalysts 195 and 197 clean and purify the slats 193 themselves, thereby keeping the slats 193 clean. The vehicle blind 191 per se has a variety of functions, such as the air-purifying function, and so on. As a result, when the vehicle blind 191 is employed, it is possible to improve the passenger-compartment environment without employing conventional air purifiers and without providing a special space for carrying conventional air purifiers. In particular, the photo-catalysts 195 and 197 can be made highly active by calcining the titanium dioxide films, and tightly attaching them to the slats 193 by calcination. Accordingly, the photo-catalysts 195 and 197 can carry out their variety of functions, like the air-purifying function, etc., more effectively.

The Thirteenth and Fourteenth Preferred Embodiments embody the present photo-catalyzer in the vehicle curtain 171 and the vehicle blind 191, respectively. The present photo-catalyzer, however, is not limited to these. For example, the present photo-catalyzer can be embodied in other light shields for a vehicle, such as a roll blind. In addition to the inner surface of the rear windshield 175 or side window 177, and to the space above the front and rear seats, the present photo-catalyzer can be disposed at any desired place in the passenger compartment where partial light-shielding is needed.

In the Thirteenth and Fourteenth Preferred Embodiments, the substrate 181 and the slats 193 working as a substrate can be formed of any arbitrary materials, such as ceramic compounds, metals, and glass, as far as the materials are inert to the photo-catalytic action, especially, to the oxidizing catalytic action of the photo-catalysts 183, 185, 195 and 197, and they can withstand calcination. Under humid or wet conditions, metallic materials are liable to be oxidized. Therefore, the substrate 181 and the slats 193 can preferably be formed of glassy materials, like a glass-fiber-woven cloth, and so on, which are chemically stable. Moreover, in the vehicle blind 191 of the Fourteenth Preferred Embodiment, a photo-catalyst identical with the photo-catalysts 195 and 197 can be disposed on portions other than the slats 193, for instance, on the supporter members 199.

Since the Thirteenth and Fourteenth Preferred Embodiments operate as a light shield for a vehicle, it is preferred that the substrate is formed of light shieldable materials. Note that, however, the substrate can be formed of materials being virtually free from a light-shielding property, namely, the substrate can be formed of substantially transparent materials. When the substrate is formed of substantially transparent materials, the resulting substrate itself allows transmission of most of the ultraviolet light shining on the passenger compartment. Consequently, the ultraviolet light can irradiate the passenger-facing surface of a photo-catalyst. As a result, such an arrangement can further facilitate the photo-catalytic action.

Fifteenth Preferred Embodiment

Figure 21:
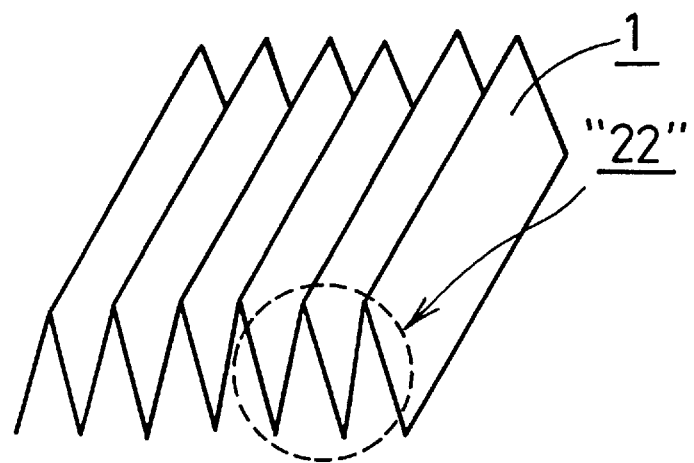
FIG. 21 is a perspective view for illustrating a Fifteenth Preferred Embodiment of the present photo-catalyzer.
Figure 22:
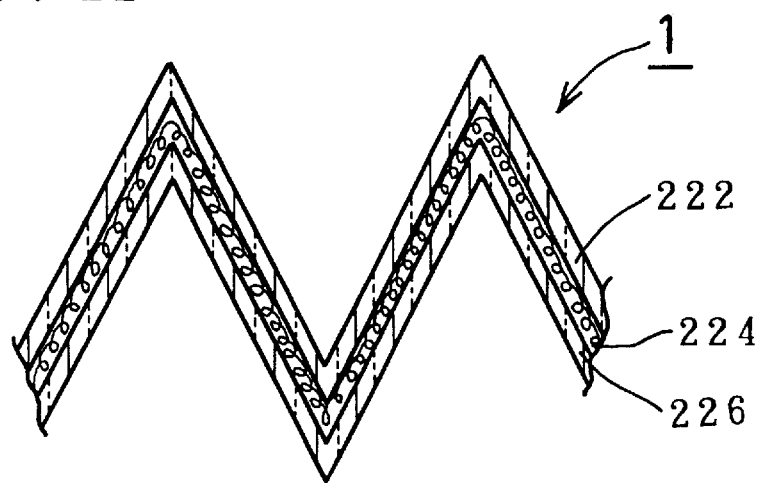
FIG. 22 is an enlarged partial cross-sectional view taken at dotted circle "22" of FIG. 21.
Figure 23:
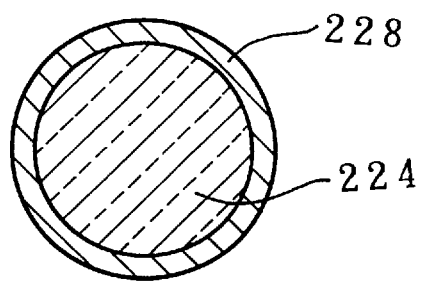
FIG. 23 is a schematic cross-sectional view for illustrating a glass yarn with an applied titanium dioxide film, the glass yarn is used in the Fifteenth Preferred Embodiment.
Figure 24:
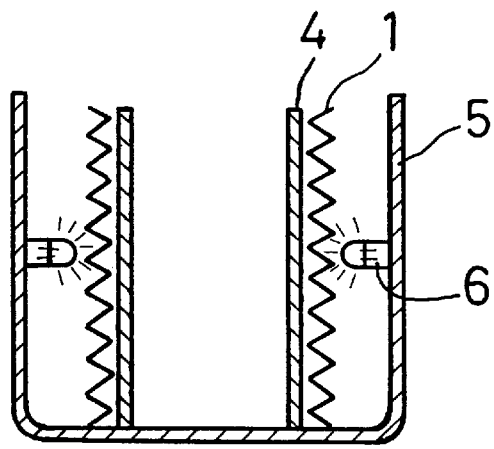
FIG. 24 is a schematic diagram for illustrating, for example, a bacteria-repelling and deodorizing apparatus or an air purifying apparatus to which the Fifteenth Preferred Embodiment is applied.

FIGS. 21 through 24 illustrate a Fifteenth Preferred Embodiment of the present photo-catalyzer. The Fifteenth Preferred Embodiment is developed in order to further improve the photo-catalytic effect of the present photo-catalyzer. FIG. 21 illustrates a perspective view of the Fifteenth Preferred Embodiment. FIG. 22 is an enlarged partial cross-sectional view of FIG. 22. FIG. 23 is a schematic enlarged cross-sectional view of a glass yarn which is used in the Fifteenth Preferred Embodiment, and on which a titanium dioxide film is disposed. FIG. 24 is a schematic cross-sectional view for illustrating how the Fifteenth Preferred Embodiment is applied to a bacteria-repelling and deodorizing apparatus, or an air purifier.

As illustrated in FIG. 21, the Fifteenth Preferred Embodiment is a filter 1 having a configuration which is prepared by folding a sheet in a zigzag manner. Specifically, as illustrated in FIG. 22, the filter 1 has a laminated construction which includes a first glass-fiber-woven cloth 222, glass yarns 224 on which a titanium dioxide film is disposed, and a second glass-fiber-woven cloth 226. As illustrated in FIG. 23, a titanium dioxide film 228 is disposed on the surface of the glass yarns 224.

The first and second glass-fiber-woven cloths 222 and 226 contact the glass yarns 224 with one of the opposite surfaces, and expose another one of the opposite surfaces to the outside. Thus, the first and second glass-fiber-woven cloths 222 and 226 hold the glass yarns 224 in a sandwich-like manner. Note that either one of the first and second glass-fiber-woven cloths 222 and 226 or both of them can be replaced by wire nets.

When ultraviolet light irradiates the glass yarns 224 on which the titanium dioxide film 228 is disposed, the titanium dioxide film 228 is activated to deodorize air and to repel bacteria. Note that the glass yarns 224 can be replaced by glass fibers, glass chips, glass rovings, glass wools, or glass papers on which the titanium dioxide film 228 is disposed.

The thus constructed filter 1 operates and produces advantages as follows: light having a wavelength of about 370 nm usually transmits through the first and second glass-fiber-woven cloths 222 and 226 because the filter 1 is transparent as a whole. Accordingly, it is possible to enhance the efficiency of irradiation onto the glass yarns 224 on which the titanium dioxide film 228 is disposed, and to eventually increase performance by using the "quantum size" effect of titanium dioxide. Moreover, it is possible to irradiate ultraviolet light onto the filter 1 from every direction, and to introduce air, or the like, into the filter 1 from every direction.

The filter 1 is flexible, and provides a high degree of configurational freedom, and a large surface area, because it is constituted by the first and second glass-fiber-woven-cloths 222 and 226, and the glass yarns 224. The titanium dioxide film 228 can be easily converted to have a highly active anatase-type crystalline structure, because the glass yarns 224 are prepared by applying the titanium dioxide film 228 on the highly heat-resistant glass yarns 224. Moreover, glass-fiber-woven cloths and glass yarns do not increase the manufacturing cost of the filter 1, because they are not expensive.

As illustrated in FIG. 24, the filter 1 can be applied to a bacteria-repelling and deodorizing apparatus, or an air purifier. For instance, the filter 1 can be wound around a retainer 4. In the peripheral wall of the retainer 4, a plurality of fine holes (not shown) are drilled so as to facilitate the flow of air, etc. The retainer 4 thus has a cylinder-shaped mesh structure as a whole, and has openings at opposite ends. The filer 1 wound around the retainer 4 is disposed in a housing 5. The housing 5 has a cylinder-shaped structure and has an opening at one of the opposite ends. On the inner peripheral surface of the housing 5, a plurality of light-emitting diodes 6 are disposed at equal intervals. Note that the housing 5 can be further provide with a lid on the top-end opening, and the light-emitting diodes 6 can be disposed on a lower surface of the lid. The operations and advantages of the thus constructed bacteria -repelling and deodorizing apparatus, or air purifier, will not be described herein, because they are identical with those of the above-described bacteria-repelling and deodorizing apparatus, or air purifiers.

Sixteenth Preferred Embodiment

Figure 25:
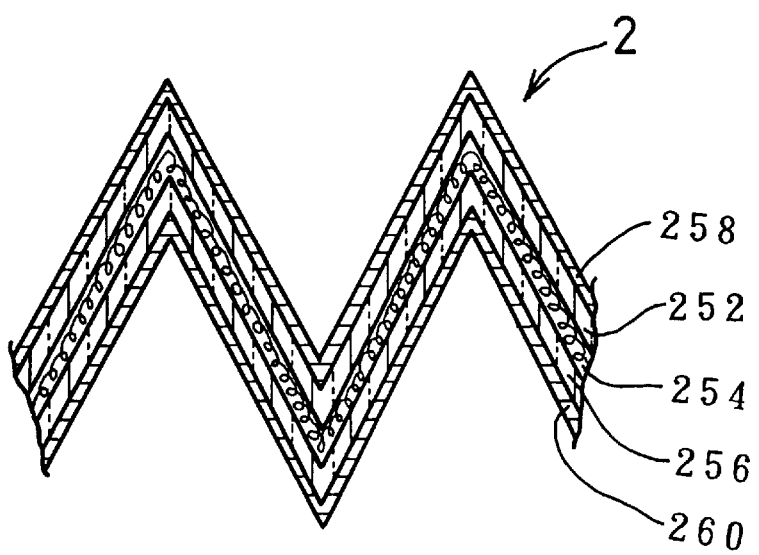
FIG. 25 is an enlarged partial cross-sectional view of a Sixteenth Preferred Embodiment of the present photo-catalyzer.
Figure 26:
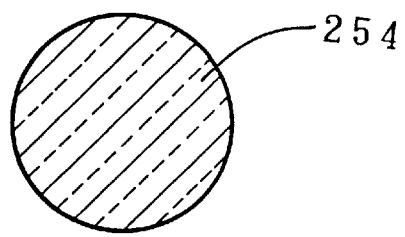
FIG. 26 is a schematic cross-sectional view for illustrating a glass yarn which is used in the Sixteenth Preferred Embodiment.

FIGS. 25 and 26 illustrate a Sixteenth Preferred Embodiment of the present photo-catalyzer. The Sixteenth Preferred Embodiment is also developed in order to further improve the photo-catalytic effect of the present photo-catalyzer. Specifically, the Sixteenth Preferred Embodiment is a modified version of the Fifteenth Preferred Embodiment. FIG. 25 is an enlarged partial cross-sectional view of the Sixteenth Preferred Embodiment. FIG. 26 is a schematic enlarged cross-sectional view of a glass yarn which is used in the Sixteenth Preferred Embodiment.

As illustrated in FIG. 25, a filter 2 according to the Sixteenth Preferred Embodiment has a laminated construction which includes a first glass-fiber-woven cloth 252, glass yarns 254, and a second glass-fiber-woven cloth 256. As hereinafter described, unlike the Fifteenth Preferred Embodiment, no titanium dioxide film is disposed on the glass yarns 254 but, instead, titanium dioxide films 258 and 260 are disposed on one of the opposite surfaces of the glass-fiber-woven-cloths 252 and 256.

As illustrated in FIG. 25, the titanium dioxide films 258 and 260 are disposed on one of the opposite surfaces of the glass-fiber-woven cloths 252 and 256 so that the films are exposed to the outside. Another of the opposite surfaces of the glass-fiber-woven cloths 252 and 256 is free from titanium-dioxide-film, and contacts with the glass yarns 254, thereby holding the glass yarns 254 in a sandwich-like manner therebetween.

As illustrated in FIG. 26, unlike the Fifteenth Preferred Embodiment, no titanium dioxide film is disposed on the surface of the glass yarn 254. Accordingly, the glass yarns 254 function as a photo-conductor or a photo-diffusing device. The glass yarns 254 can be prepared in an arbitrary amount with respect to the amount of the titanium dioxide films 258 and 260 so that they enable the titanium dioxide films 258 and 260 to effect desired deodorizing and bacteria-repelling actions. Instead of the glass yarns 254, it is possible to employ glass fibers, glass chips, glass rovings, glass wools, aluminum yarns, aluminum fibers, aluminum chips, aluminum rovings, or aluminum wools.

When ultraviolet light irradiates the thus constructed filter 2, some of the irradiated ultraviolet light enters the glass yarns 254, transmits through the first and second glass-fiber-woven cloths 252 and 256, and irradiates the titanium dioxide films 258 and 260 disposed on the external surfaces of the first and second glass-fiber-woven cloths 252 and 256. Thus, the ultraviolet light irradiates both external and internal surfaces of the titanium dioxide films 258 and 260. Consequently, in the filter 2, the ultraviolet light irradiates titanium dioxide films 258 and 260 over a remarkably enlarged surface area.

Except for the operation and advantages effected by the glass yarns 254, the operation and advantages of the filter 2 are identical with those of the filter 1 according to the Fifteenth Preferred Embodiment. Therefore, they will not be described herein.

Seventeenth Preferred Embodiment

Figure 27:
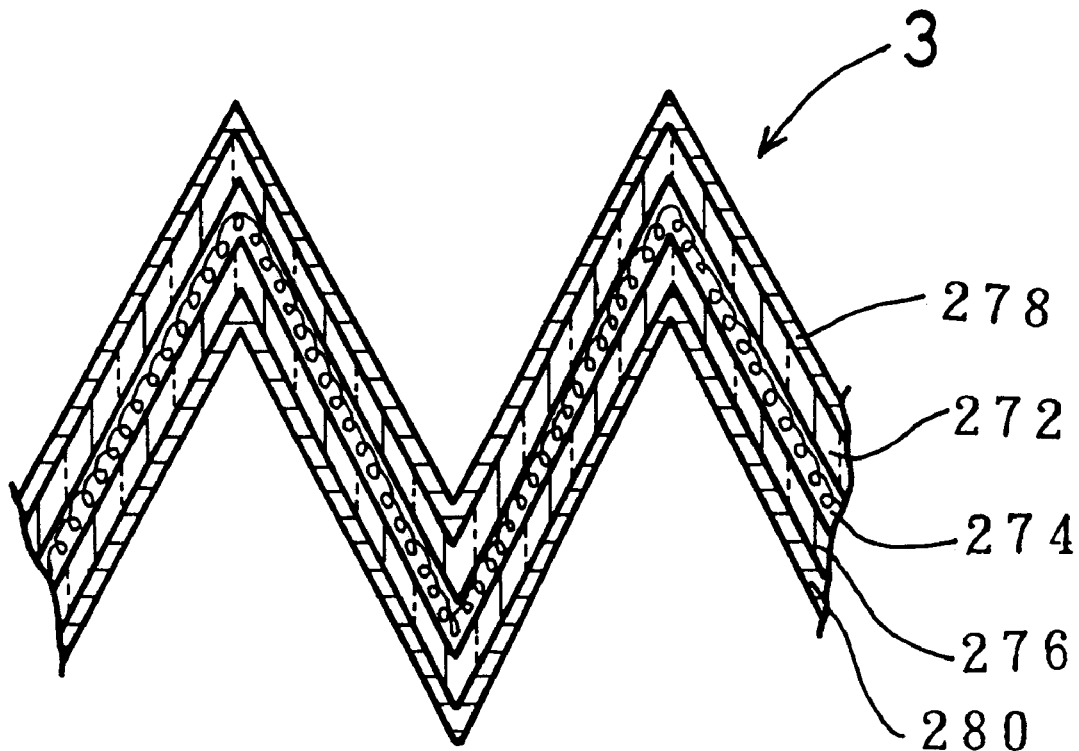
FIG. 27 is an enlarged partial cross-sectional view of a Seventeenth Preferred Embodiment of the present photo-catalyzer.
Figure 28:
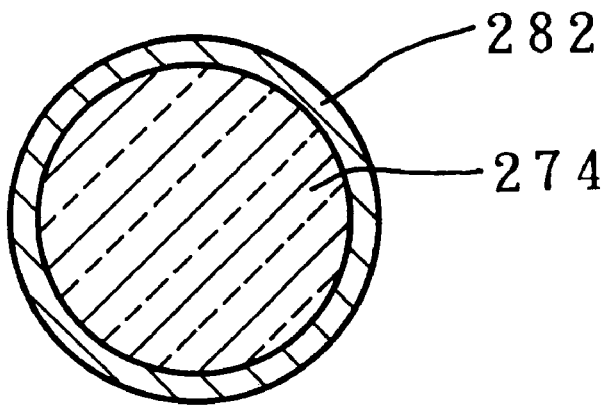
FIG. 28 is a schematic cross-sectional view for illustrating a fiber with a silver film-coated fiber which is used in the Seventeenth Preferred Embodiment.

FIGS. 27 and 28 illustrate a Seventeenth Preferred Embodiment of the present photo-catalyzer. The Seventeenth Preferred Embodiment is also developed in order to further improve the photo-catalytic effect of the present photo-catalyzer. The Seventeenth Preferred Embodiment is also a modified version of the Fifteenth Preferred Embodiment. FIG. 27 is an enlarged partial cross-sectional view of the Seventeenth Preferred Embodiment. FIG. 28 is a schematic enlarged cross-sectional view of a silver-covered fiber which is used in the Seventeenth Preferred Embodiment.

As illustrated in FIG. 27, a filter 3 according to the Seventeenth Preferred Embodiment has a laminated construction which includes a first glass-fiber-woven cloth 272, silver-coated fibers 274, and a second glass-fiber-woven cloth 276. As hereinafter described, unlike the Fifteenth Preferred Embodiment, silver-coated fibers 274 are used instead of the glass yarns 224 on which the titanium dioxide film 228 is disposed, and titanium dioxide films 278 and 280 are disposed on one of the opposite surfaces of the glass-fiber-woven-cloths 272 and 276.

As illustrated in FIG. 27, the titanium dioxide films 278 and 280 are disposed on one of the opposite surfaces of the glass-fiber-woven cloths 272 and 276 so that the films are exposed to the outside. Another of the opposite surfaces of the glass-fiber woven cloths 272 and 276 is free from titanium-dioxide-film, and contacts with the silver-coated fibers 274, thereby holding the silver-coated fibers 274 in a sandwich-like manner therebetween.

As illustrated in FIG. 28, unlike the Fifteenth Preferred Embodiment, the fibers 274 coated with silver 282 are used in the filter 3, instead of the glass yarns 224 on which the titanium dioxide film 228 is disposed. Accordingly, the fibers 274 with silver coating function as a device for reflecting ultraviolet light, or the like. Instead of silver, it is possible to coat the fibers 274 with other noble metals, such as gold (Au) platinum (Pt), rhodium (Rh), or palladium (Pd). Moreover, in addition to the fibers 274, it is possible to coat a wire net, or the like, with the metals by a plating or vapor-depositing process.

When ultraviolet light, etc., shines on the thus constructed filter 3, the ultraviolet light irradiates the external surfaces of the titanium dioxide films 278 and 280. Some of the ultraviolet light reaches the silver-coated fibers 274, and is reflected by the silver coating 282. The reflected ultraviolet light transmits through the first and second glass-fiber-woven cloths 272 and 276, and this time irradiates the internal surface of the titanium dioxide films 278 and 280. Thus, the ultraviolet light irradiates both external and internal surfaces of the titanium dioxide films 278 and 280. Consequently, in the filter 3, not only does the ultraviolet light irradiate the titanium dioxide films over a remarkably enlarged surface area, but also it irradiates onto them with an extremely high irradiation efficiency.

Excepting the operations and advantages effected by the fibers 274 coated the silver 282, the operation and advantages of the filter 3 are identical with those of the filter 1 according to the Fifteenth Preferred Embodiment. Therefore, they will not be described herein.

Eighteenth Preferred Embodiment

Figure 29:
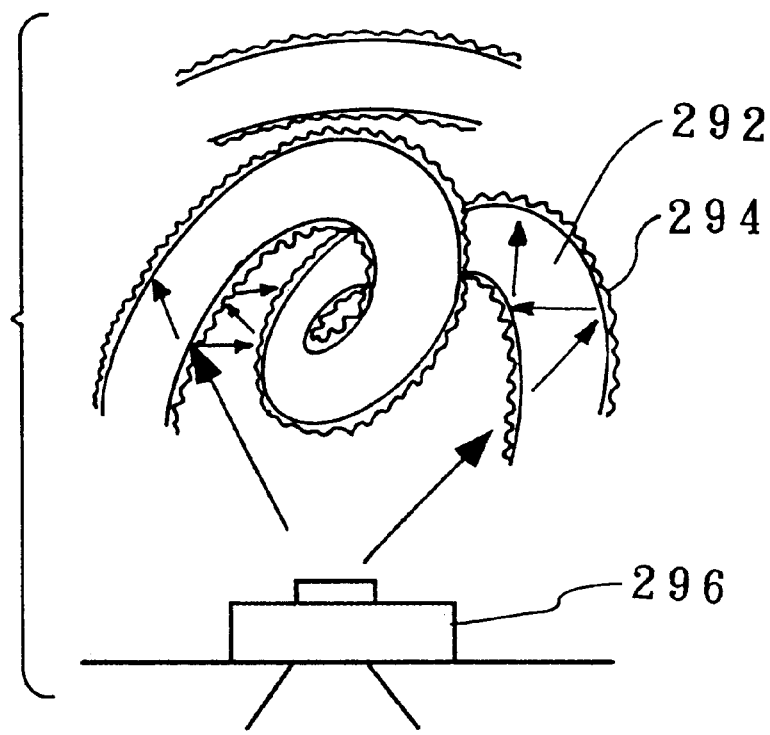
FIG. 29 is a schematic diagram for illustrating the operation of an Eighteenth Preferred Embodiment of the present photo-catalyzer.

As illustrated in FIG. 29, an Eighteenth Preferred Embodiment of the present photo-catalyzer comprises a bulky support 292, a photo-catalyst 294, and a light-emitting diode 296. The bulky support 292 includes fibers. The photo-catalyst 294 is disposed on the bulky support 292. When the light-emitting diode 296 irradiates light onto the bulky support 292 and the photo-catalyst 294, the photo-catalyst 294 is activated. As a result, the photo-catalyst 294 removes odor components and destroys micro-organisms, such as fungi or bacteria, by decomposition. The odor components, etc., exist in the atmosphere where the bulky support 292 is present.

The bulky support 292 includes fibers, and accordingly has an extremely large surface area. When ultraviolet light is reflected or diffused by a surface of one of the fibers constituting the bulky support 292, the ultraviolet light irradiates neighboring fibers. Therefore, the irradiated ultraviolet light can be utilized effectively, and the photo-catalyst 294 is improved in terms of reaction efficiency. The bulky support 292 is lightweight and has a high degree of configurational freedom. Hence, even when the bulky support 292 has to be placed in small and complicated locations, it can easily conform to the configuration of such locations. Thus, the Eighteenth Preferred Embodiment of the present invention can offer a wide variety of applications.

As for the fibers constituting the bulky support 292, it is possible to appropriately select at least one member from the group consisting of organic fibers, inorganic fibers, and carbon fibers. The organic fibers can be synthetic-resin fibers, etc. The inorganic fibers can be glass fibers, metallic fibers, and so on. The fibers can be crystalline. It is possible to employ whiskers as the fibers.

Moreover, the fibers constituting the bulky support 292 can preferably be transparent so that ultraviolet light can be transmitted. As for transparent fibers, it is possible to exemplify glass fibers and synthetic-resin fibers. When transparent fibers are employed, ultraviolet light irradiates such fibers as illustrated in FIG. 29, reflection and diffusion occur more frequently in such fibers. Consequently, ultraviolet light irradiates the photo-catalyst 294 at a higher rate than without the reflection and diffusion effects, and further enhances the catalytic activity of the photo-catalyst 294.

In addition, the photo-catalyst 294 may be subjected to heat in an application process, or the present photo-catalyzer may be used at elevated temperatures. If such is the case, synthetic-resin fibers may be insufficient in terms of heat resistance. Hence, in such applications, glass fibers can be employed preferably.

As the glass fibers, alkaline glass fibers may hinder the photo-catalyst 294 from being applied. Therefore, it is preferred to employ alkaline-free glass fibers. It has been known that glass fibers can be formed in a variety of shapes, for example, in cloth, roving, yarn, or the like. The glass fibers can preferably have a shape which makes application of the photo-catalyst 2 easier, which has a large surface area, which is likely to be bulky, and which enables easy manufacture. Table 1 below lists various glass fibers and summarizes their characteristics.

TABLE 1

| | Application | Surface Area | Manufacture | Overall Evaluation |
|---|---|---|---|---|
| Cloth | ++ | + | ++ | ++ |
| Roving | + | + | + | + |
| Chopped Strand | − | ++ | − | − |
| Chopped-Strand Mat | + | + | + | + |
| Glass Wool | + | ++ | + | + |
| Roving Cloth | + | + | + | + |
| Yarn (Twisted) | ++ | ++ | ++ | +++ |
| Yarn (Not Twisted) | + | − | − | − |
| Yarn (Others) | + | ++ | + | ++ |
| Glass Paper | + | ++ | + | ++ |

(Note):
+++ designates "Very Good".
++ designates "Good".
+ designates "Fair".
− designates "Poor".

It is understood from Table 1 that it is preferred to employ twisted glass yarns. Among twisted glass yarns, it is especially preferred to choose slivered glass yarns, whose surface is fluffed, and bulky glass yarns because they have an extremely large surface area. The surface of the glass yarns can be fluffed by a mechanical process, an acidifying process, or an alkalinizing process. Note that the diameter of individual fibers constituting the glass yarns is not limited in particular. However, in view of assuring high gas permeability and easy application of the photo-catalyst 294, the diameter of individual fibers can preferably fall in a range from 45 to 500 tex. In order to provide a large surface area, the number of twistings can preferably fall in a range from 1 to 5 turns.

As for the photo-catalyst 294, $TiO_2$, $WO_3$, CdS, $SrTiO_3$, and $MOS_2$ can be used. In view of safety and photo-chemical activity, it is especially preferred to employ $TiO_2$. Concerning the crystalline structure of $TiO_2$, it is possible to employ either a rutile-type crystalline structure or an anatase-type crystalline structure, but it is especially preferred to employ an anatase-type crystalline structure which exhibits a greater catalytic activity.

Regarding a process for applying the photo-catalyst 294, particles of the photo-catalyst 294 can be scattered, or the photo-catalysts 294 can be applied as a film. When applying the photo-catalyst 294 as a film, it is preferred to apply the film as transparently as possible. If such is the case, ultraviolet light irradiates the fibers of the bulky support 292, and reflects and diffuses therein as illustrated in FIG. 29. The reflected and diffused ultraviolet light then irradiates the photo-catalyst 294 disposed on neighboring fibers. As a result, the ultraviolet light is more efficiently utilized and, accordingly, the photo-catalyst 294 exhibits a further enhanced catalytic activity.

Even when the photo-catalyst 294 is used in a trace amount, the photo-catalyst 294 can exhibit photo-catalytic action. In practice, it is preferred to apply the photo-catalyst 294 in an amount from 10 to 40 parts by weight with respect to 100 parts by weight of the bulky support 292. When the photo-catalyst 294 is used in an amount of more than 40 parts by weight with respect to 100 parts by weight of the bulky support 292, not only does the photo-catalyst 294 exhibit a saturated catalytic effect, but also it is less likely to adhere to the bulky support 292. In addition, using such a large amount makes the photo-catalyst 294 more susceptible to thermal shock, and accordingly the strength of the photo-catalyst 294 may decrease.

The photo-catalyst 294 can be loaded on the bulky support 292 by the following processes: a slurry of the photo-catalyst 294 can be deposited and calcined on the bulky support 292, and the photo-catalyst 294 can be deposited on the bulky support 292 by a physical vapor deposition (PVD) process like sputtering or by a chemical vapor deposition (CVD) process. Note that the finer the particle diameter of the photo-catalyst 294, the more the catalytic activity of the photo-catalyst 294 is improved. Accordingly, when a slurry of the photo-catalyst 294 is deposited and calcined on the bulky support 292, it is preferred to employ a sol of the photo-catalyst 294.

Moreover, it is preferred to composite the photo-catalyst 294 with a metal co-catalyst. The metal co-catalyst can be silver (Ag), copper (Cu), platinum (Pt), palladium (Pd), or rhodium (Rh). The metal co-catalyst attracts electrons to further enhance the catalytic activity of the photo-catalyst 294. If such is the case, the photo-catalyst 294 can destroy or repel micro-organisms, such as fungi or bacteria, without the irradiation of ultraviolet light.

The metal co-catalyst can be composited with the photo-catalyst 294 by the following processes: the metal co-catalyst can be deposited on the photocatalyst 294 by a sputtering or plating process, the metal co-catalyst can be coated on a film of the photo-catalyst 294, the metal co-catalyst can be deposited on the bulky support 292 together with the photo-catalyst 294, and fibers on which the metal co-catalyst is disposed can be mixed with fibers on which the photo-catalyst 294 is disposed. When the metal co-catalyst is composited in an amount from 0.05 to 0.5% by weight, preferably 0.1% by weight, with respect to the photo-catalyst 294, the metal co-catalyst can satisfactorily provide the above advantage.

As for the light-emitting diode 296 producing ultraviolet light having a wavelength from 360 to 400 nm, it is optimal to employ a gallium nitride (GaN)-based photo-semiconductor crystal having a p-n junction. When this light-emitting diode is employed, it is possible not only to effectively utilize the ultraviolet emission, but also to downsize the Eighteenth Preferred Embodiment of the present photo-catalyzer. Accordingly, it is possible to use the Eighteenth Preferred Embodiment conveniently.

The light-emitting diode 296 is not only a small light-emitting device, but it can also be operated at low voltage. Consequently, it can be actuated to emit light with a dry-cell battery. Therefore, it does not require a large space for its installation. Thus, the Eighteenth Preferred Embodiment of the present photo-catalyzer can be easily used anywhere, including small places. In addition, the whole Eighteenth Preferred Embodiment, including the bulky support 292 on which the photo-catalyst 294 is disposed, can be downsized to a compact structure.

Moreover, it is preferred that the light-emitting diode 296 barely emits ultraviolet light harmful to the human body, for instance, the far ultraviolet (e.g., UV-B or UV-C) having a wavelength of 320 nm or less. In view of light-emitting efficiency and electricity consumption, the light-emitting diode 296 preferably produces light having a wavelength falling in a spectrum range from 360 to 400 nm only.

In actual applications, contrary to semi-conductor lasers, light-emitting diodes generally produce light whose wavelength spreads over at least 50 nm. Accordingly, it is difficult to provide a light-emitting diode capable of producing light whose wavelength falls in a range from 360 to 400 nm only. Hence, light-emitting diodes generally produce visible light as well. When a light-emitting diode produces visible light, it is possible to tell that the light-emitting diode is operating. In addition, when such light-emitting diodes produce visible light which exhibits bright and vivid colors, the light-emitting diodes can produce an illuminating or displaying effect. Note that, however, even when light (or ultraviolet light) has a wavelength of 400 nm or less, light having a wavelength of about 380 nm produces a blurry background in dark purple, for example. Therefore, even when light-emitting diodes produce light having a wavelength of 400 nm or less only, the emitted light is not black light completely, but is usually visible.

In addition to the bulky support 292, it is possible to employ a porous support including a transparent material. As for the porous support, it is possible to exemplify a glass filter, foamed glass, and so on. Similar to the bulky support, the porous support has a large surface area. Likewise, the porous support reflects and diffuses the incident ultraviolet light thereon, because it is transparent and does not absorb light. Consequently, a photo-catalyst disposed on the porous support exhibits an enhanced catalytic activity. Thus, the porous support operates effectively and provides advantages like the bulky support.

Even when the porous support is employed, the aforementioned specific photo-catalysts can be employed and can be loaded on the porous support in the same amount as they are loaded on the bulky support. Moreover, the other constituent components, like the above-described light-emitting diodes, can be identical with those of the Eighteenth Preferred Embodiment of the present photo-catalyzer, including the bulky support.

(Product Evaluation)

A glass yarn was prepared. The glass yarn had a fiber diameter of 75 tex and was twisted by 3 turns (i.e., "75-tex"×"3-turn"="245-count"). The glass yarn was made from "E glass", which was produced by NITTO BOSEKI Co., Ltd., and had a filament diameter of 9 $\mu$m. Note that "E glass" was alkaline-free glass. The glass yarn was immersed in an anatase-type titania sol having a $TiO_2$ concentration of 20% by weight and was then blown to remove excess sol. The titania sol was "STS-2", produced by ISHIHARA SANGYOU Co., Ltd., The glass yarn with the titania sol deposited thereon was dried at 150° C. for 2 hours and calcined at 500° C. for 2 hours. The above-described steps were carried out repeatedly a couple of times. Thus, a $TiO_2$ coating layer was applied on the surface of the glass yarn in an amount of 25 parts by weight with respect to 100 parts by weight of the glass yarn.

Figure 30:
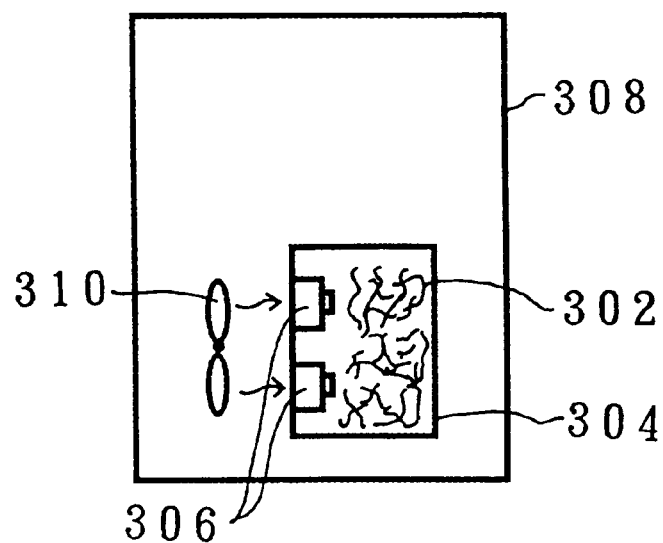
FIG. 30 is a schematic diagram for illustrating how the Eighteenth Preferred Embodiment was examined in a product evaluation.

Four grams of the resulting bulky support 302, on which the TiO$_2$ coating layer was disposed, was placed in a netted container 304 adjacent to ten light-emitting diodes 306 as illustrated in FIG. 30. A photo-catalyzer was thus prepared.

Figure 31:
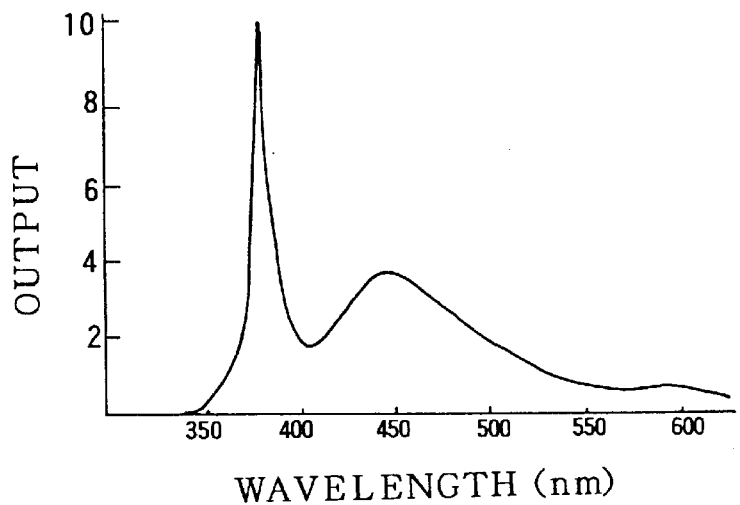
FIG. 31 is a graph for illustrating the distribution of light wavelengths emitted from a light-emitting diode which was used in the Eighteenth Preferred Embodiment and the product evaluation.

The light-emitting diodes 306 were small devices, and comprised a tip and a molded lens. The tip included a gallium nitride (GaN)-based photo-semiconductor crystal having a p-n junction and emitting light. The molded lens enclosed the tip therein and gave the emitted light direction. As illustrated in FIG. 31, the light-emitting diodes 306 produced ultraviolet light having a wavelength from 360 to 400 nm as well as visible light having a wavelength of 450 nm. Thus, the light-emitting diodes 306 produced an intense blue color.

Figure 32:
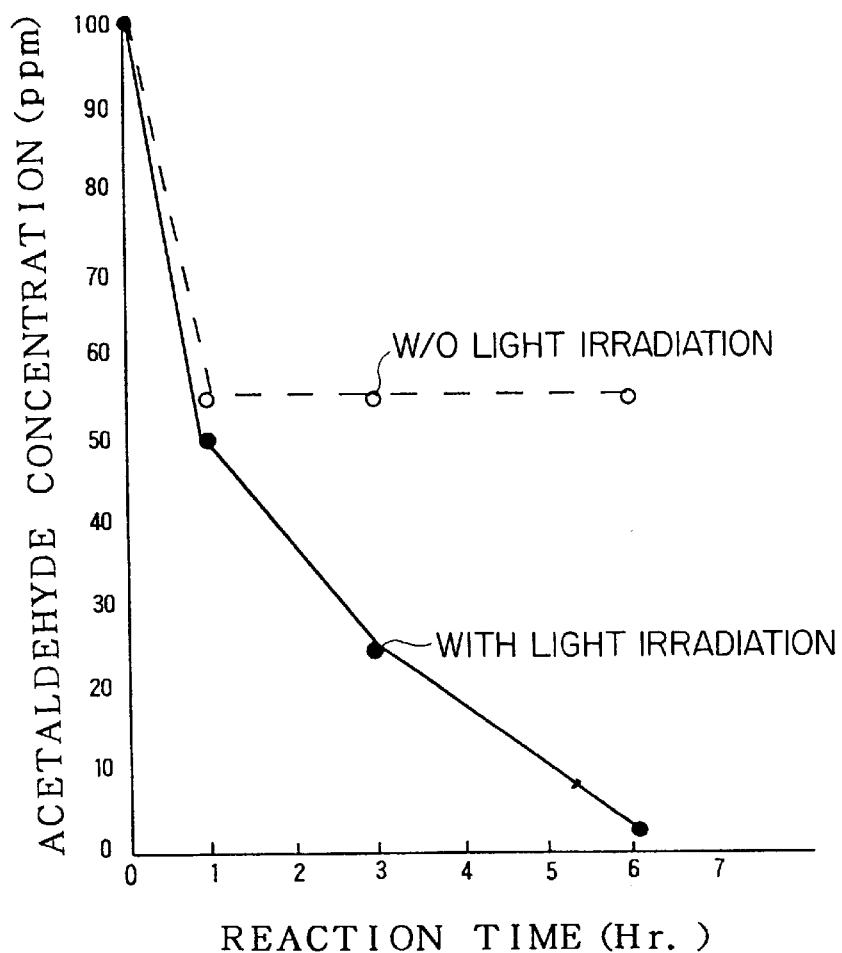
FIG. 32 is a graph for illustrating a permanent change of acetaldehyde concentration in the product evaluation, closed circles are the results with light irradiation and open circles are the results without light irradiation.

As illustrated in FIG. 30, the photo-catalyzer was placed in an enclosable reaction container 308 having a volume of 3 L. After substituting the air in the container 308 with a gas, the container 308 was closed. The substituent gas included acetaldehyde in an amount of 100 ppm. While a fan 310 moved the gas around the photo-catalyzer, the light-emitting diodes 306 were turned on to emit light. A stable change in acetaldehyde concentration was measured. FIG. 32 illustrates the results of the measurement. This type of measurement was repeated, except that the light-emitting diodes 306 were turned off so as not to emit light, and FIG. 32 illustrates the results of this extra measurement.

As illustrated in FIG. 32, the acetaldehyde concentration was permanently decreased when the light-emitting diodes 306 produced light. It is thus apparent from FIG. 32 that the photo-catalyst (i.e., TiO$_2$ coating layer) caused the decomposition of the acetaldehyde. Note that, when the light-emitting diodes 306 did not produce light, the acetaldehyde concentration initially decreased. This phenomenon is assumed to result from the adsorption of the acetaldehyde to the bulky support 302 on which TiO$_2$ was disposed. Accordingly, when the light-emitting diodes 306 did not produce light, the acetaldehyde concentration stabilized after the adsorption to the bulky support 302 was saturated. Thus, no decomposition of the acetaldehyde occurred when the photo-catalyzer was not activated by light.

Nineteenth Preferred Embodiment

Figure 33:
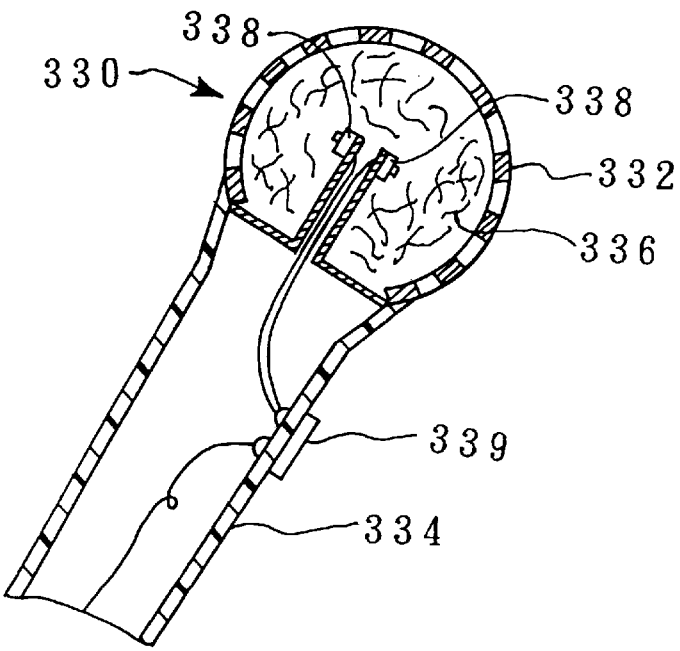

In a Nineteenth Preferred Embodiment, the present photo-catalyzer is built into a moving-coil microphone. As illustrated in FIG. 33, a microphone 330 comprises a spherical outer frame 332 and a grip 334. The outer frame 332 includes a wire net. The grip 334 is connected to the outer frame 332 and includes a resin. The present photo-catalyzer is accommodated in the outer frame 332.

As illustrated in FIG. 33, the inside of the outer frame 332 is filled with a bulky support 336 on which TiO$_2$ is disposed. Two light-emitting diodes 338 are attached back-to-back, and are disposed in the middle of the bulky support 336. The bulky support 336 and light-emitting diodes 338 are similar to those provided in the above-described product evaluation. In the outer frame 332, there is further disposed a voice-current converter (not shown). The voice-current converter includes a vibrator plate made of Duralumin (Trade Mark), an aluminum alloy. Note that the bulky support 336 and light-emitting diodes 338 are disposed in the outer frame 332 so as not to interfere with the voice-current converter.

In the grip 334 of the microphone 330, there is accommodated a dry-cell battery (not shown) which is a power source for the microphone 330 itself. The dry-cell battery may also be a power source for the light-emitting diodes 338. The grip 334 is further provided with a switch 339 for turning on and off the voice-current converter. Simultaneous with the turning on and off of the voice-current converter, the switch 339 turns on and off the light-emitting diodes 338 as well.

In the Nineteenth Preferred Embodiment, the switch 339 is turned on to allow the light-emitting diodes 338 to produce ultraviolet light having a wavelength from 360 to 400 nm. The ultraviolet light irradiates the bulky support 336 on which TiO$_2$ is disposed, thereby decomposing and removing odors or destroying micro-organisms which may be present in the outer frame 332 by means of the photo-catalytic action of TiO$_2$. Thus, it is possible to comfortably use the microphone 330 as a microphone capable of deodorizing and destroying micro-organisms.

In addition, the light-emitting diodes 338 produce blue visible light. The blue visible light passes outside through clearances in the bulky support 336 on which TiO$_2$ is disposed and through the outer frame 332, and can be seen on the outside. Thus, it is possible to immediately tell whether the microphone 330 and the built-in photo-catalyzer are turned on or off. Moreover, the blue visible light can enrich the atmosphere surrounding the user of the microphone.

It is furthermore preferred to dispose a fan in the grip 334 to forcibly move air in and out of the bulky support 336 on which TiO$_2$ is disposed. Thus, oxygen is continuously supplied to the bulky support 336 on which TiO$_2$ is disposed. As a result, the microphone 330 can more reliably decompose and remove odors and destroy micro-organisms.

When the outer frame 332 is plated with silver, the bacteria-repelling action of silver is added to the repelling action of the built-in present photo-catalyzer. As a result, it is possible to use the microphone 330 more comfortably. Note, alternatively, that the TiO$_2$ can be disposed on the outer frame 332.

Twentieth Preferred Embodiment

Figure 34:
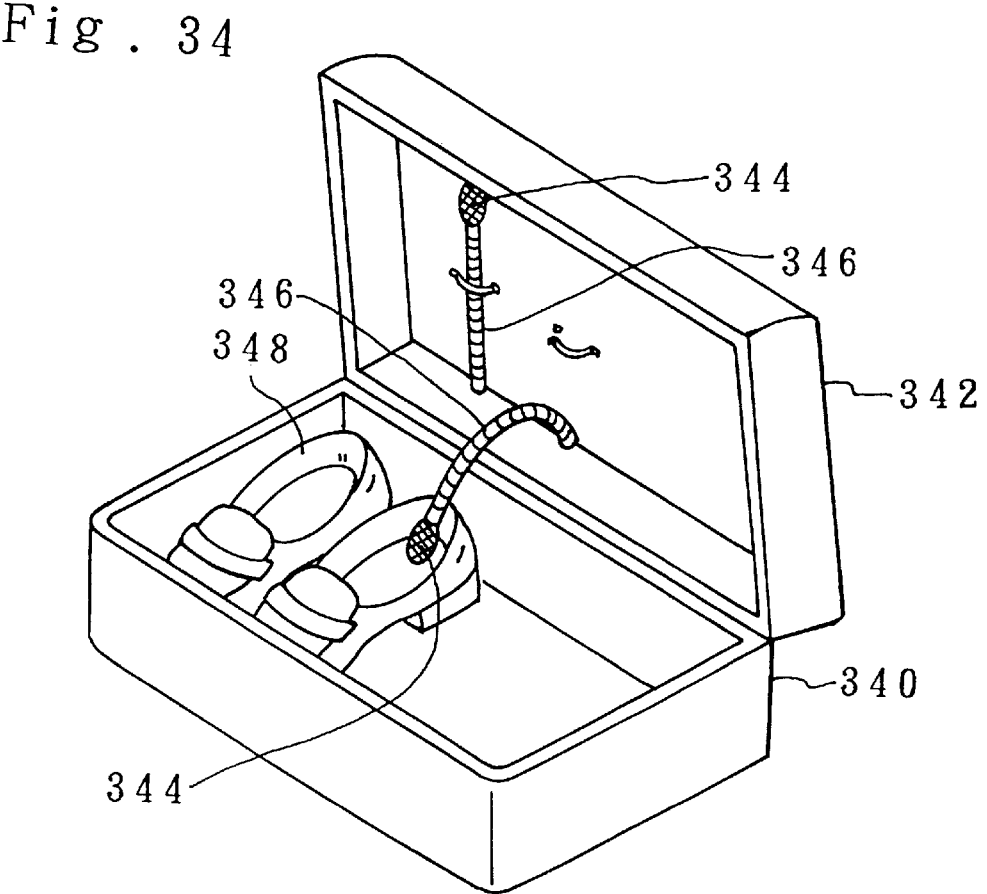
FIG. 34 is a perspective view for illustrating a shoe container which is provided with a Twentieth Preferred Embodiment of the present photo-catalyzer.

A Twentieth Preferred Embodiment of the present photo-catalyzer is an application of the invention provided in a shoe container, as illustrated in FIG. 34.

As illustrated in FIG. 34, the Twentieth Preferred Embodiment of the present photo-catalyzer is disposed in a lid 342 of a shoe container 340. The Twentieth Preferred Embodiment comprises a substantially spherical head member 344 and a leg member 346 connected to the head member 344. The head member 344 is made of a wire net. The leg member 346 is made freely bendable.

In the head member 344 of the Twentieth Preferred Embodiment of the present photo-catalyzer, there is filled a bulky support (not shown) on which TiO$_2$ is disposed. The construction of the bulky support is similar to that of the Nineteenth Preferred Embodiment, and accordingly will not be detailed herein. Likewise, in the middle of the bulky support, there are disposed a pair of light-emitting diodes (not shown). The lid 342 is provided with a built-in dry-cell battery (not shown) and a switch (not shown). The dry-cell battery supplies electricity to the light-emitting diodes. The switch turns on and off the light-emitting diodes. When the switch is turned on, electricity is supplied to the light-emitting diodes.

The Twentieth Preferred Embodiment operates as follows. A pair of shoes 348 are accommodated in the shoe container 340. The lid 342 is closed and the head member 344 of the present photo-catalyzer is placed in the shoes 348. The switch is then turned on to allow the light-emitting diodes produce ultraviolet light. The ultraviolet light shines on the bulky support on which TiO$_2$ is disposed. Thus, odors from the shoes 348 are decomposed and removed by the oxidative action of the photo-catalyzer.

In the Twentieth Preferred Embodiment, a dry-cell battery is used as a power source. Note that, when the Twentieth Preferred Embodiment is applied to automobiles, an automobile battery can be used as a power source.

Twenty-first Preferred Embodiment

Figure 35:
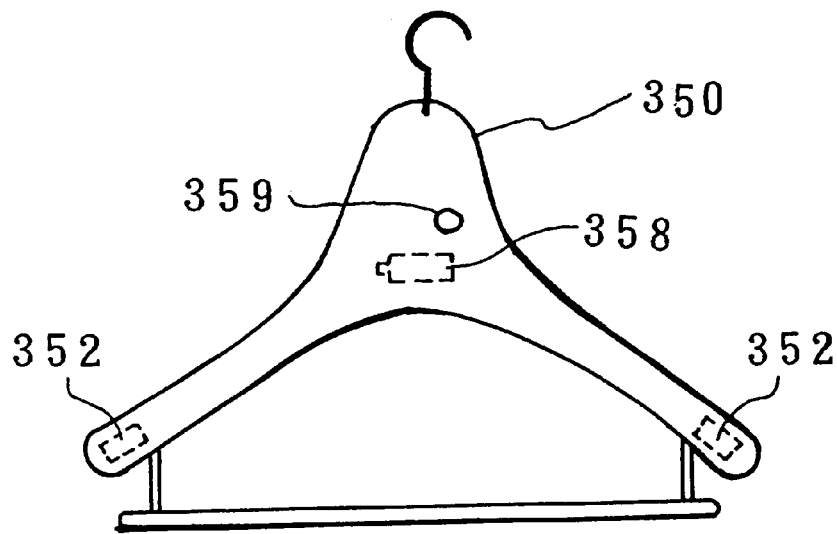

A Twenty-first Preferred Embodiment of the present photo-catalyzer is an application of the invention provided in a hanger, as illustrated in FIG. 35.

Figure 36:
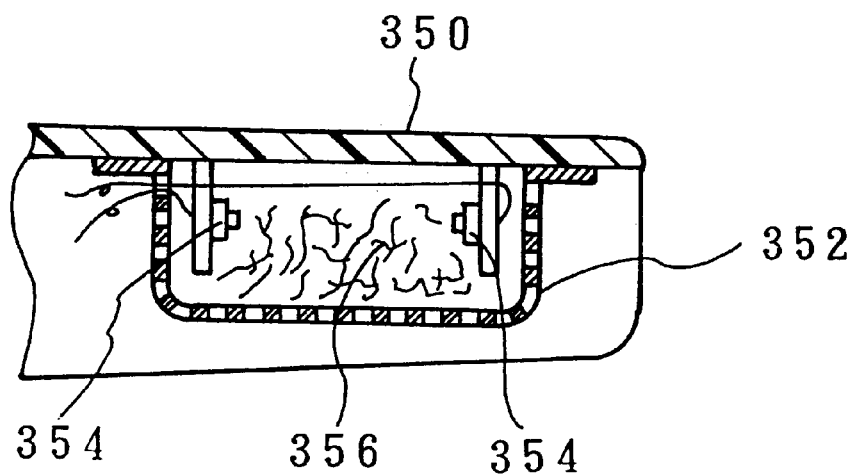
FIG. 36 is an enlarged cross-sectional view for illustrating major portions of the clothing hanger depicted in FIG. 35.

As illustrated in FIG. 35, in the Twenty-first Preferred Embodiment of the present photo-catalyzer, a hanger 350 is provided with an opposing pair of containers 352 at the lower ends. The containers 352 are exposed to the outside and include a net member made from resin. In the container 352, there is filled a bulky support on which TiO$_2$ is disposed. The construction of the bulky support is similar to that of the Nineteenth Preferred Embodiment. As illustrated in FIG. 36, on opposing inner sides of the container 352 there are disposed a pair of light-emitting diodes 354 to supply ultraviolet light to the bulky support 356. At the center of the hanger 350, there is incorporated a dry-cell battery 358. The hanger 350 is also provided with a switch 359 for turning on and off the light-emitting diodes 354. Thus, when the switch 359 is turned on, electricity is supplied from the dry-cell battery 358 to the light-emitting diodes 354.

The Twenty-first Preferred Embodiment operates as follows. Clothing, a jacket for example, is put on the hanger 350. The switch 359 is then turned on to allow the light-emitting diodes 354 to produce light. The ultraviolet light is irradiated onto the bulky support 356 on which TiO$_2$ is disposed, thereby decomposing and reducing bad odors which result from the sleeves of the jacket being in contact with the armpits of the human body.

Modified Versions of the Preferred Embodiments

As earlier described, the present photo-catalyzer can be provided in automobile console boxes, in air cleaners, in air conditioners, adjacent to filters, etc. In addition to the preferred embodiments described above, the present photo-catalyzer can be provided in the lid of garbage containers, in a slippers stand adjacent to the inside of slippers, and on a footrest in automobile passenger compartments. The present photo-catalyzer is so compact that it can be employed in many places, virtually without limit. Hence, the present photo-catalyzer can be utilized in various fields.

In particular, in the Nineteenth through Twenty-first Preferred Embodiment, the support on which TiO$_2$ is disposed is made from formless glass yarns. The present photo-catalyzer is not limited thereto. For instance, in order to prepare the support on which TiO$_2$ is disposed, it is possible to employ a sheet of glass cloth as a support per se, and to dispose TiO$_2$ thereon. If such is the case, the present photo-catalyst can be used in other applications.

For example, such a sheet-shaped support on which TiO$_2$ is disposed can be applied to an automobile sunlight-shielding screen which can be wound up in a roll and a pair of light-emitting diodes can be further disposed at opposite ends of the rolled-up sheet-shaped support. In the daytime, the thus constructed present photo-catalyzer can be used not only as a sunlight-shielding screen, but also as a deodorizing apparatus, namely, when the sunlight shines on the unrolled sheet-shaped support and activates TiO$_2$, an automobile passenger compartment can be deodorized. In the nighttime, the light-emitting diodes are turned on while the sheet-shaped support is rolled up. The ultraviolet light produced by the light-emitting diodes can be efficiently irradiated onto the rolled-up sheet-shaped support. Thus, in the nighttime as well, the automobile passenger compartment can be deodorized.

Moreover, when the present photo-catalyzer comprises a sheet-shaped support on which TiO$_2$ is disposed and a light-emitting diode is disposed to face one of the opposite surfaces of the sheet-shaped support, the photo-catalyzer can be utilized in various applications: as a deodorizing sheet to be placed in an automobile luggage compartment, a deodorizing carpet, a deodorizing sun visor, and so on.

The photo-catalyzer of the present invention has been disclosed in foreign patent applications JP 7-192829, JP 7-192821, JP 7-192819, JP 7-195576, JP 7-195573, and JP 7-195572, the entire contents of which are hereby incorporated by reference and relied upon.

Having now fully described the present invention, it will be apparent to one of ordinary skill in the art that many changes and modifications can be made thereto without departing from the spirit or scope of the present invention as set forth herein including the appended claims.

What is claimed is:

1. A photo-catalyzer comprising:
    a substrate;
    a titanium dioxide film disposed on a portion of said substrate, said titanium dioxide film providing a photo-catalyst; and
    a light-emitting diode including a gallium nitride (GaN)-based photo-semiconductor crystal having a p-n junction, and disposed adjacent said titanium dioxide film to irradiate said titanium dioxide film with an ultraviolet light at a wavelength ranging from about 360 to 400 nm.

2. The photo-catalyzer according to claim 1, wherein said photo-catalyzer is a bactericidal and deodorizing apparatus, and wherein
    said substrate is constructed and arranged as a housing supporting said light-emitting diode and having an inner surface at least a portion of which defines an accommodation chamber thereon,
    said titanium dioxide film is disposed on a portion of said inner surface.

3. The photo-catalyzer according to claim 1, wherein said photo-catalyzer is an air purifying apparatus for an air conditioning apparatus, said air conditioning apparatus comprising:
    a duct having an air inlet port and an air outlet port,
    an air temperature control system disposed adjacent said duct to vary temperature of air flowing within said duct, and
    an air blower having a fan disposed in the duct;
    wherein a surface of said substrate is in contact with air flowing in said duct and said titanium dioxide film is disposed on at least a portion of said surface, said titanium dioxide film and said light-emitting diode comprising said air purifying apparatus.

4. The photo-catalyzer according to claim 3, wherein the surface of said substrate is an inner surface of the duct.

5. The photo-catalyzer according to claim 3, wherein the fan has a plurality of blades, each blade having opposing surfaces, and wherein the surface of said substrate is the opposing surfaces of each fan blade.

6. The photo-catalyzer according to claim 3, further comprising:
   a honeycomb-shaped support disposed in said duct, said honeycomb-shaped support including an end surface and a plurality of cellular walls defining a plurality of through bores having an inner surface;
   wherein said surface comprises at least a portion of said end surface and at least a portion of said inner surface, and
   wherein said light-emitting diode irradiates ultraviolet light onto said end surface.

7. The photo-catalyzer according to claim 1, wherein said substrate is a bulky support including fibers.

8. The photo-catalyzer according to claim 7, wherein the fibers are formed from a material selected from the group consisting of transparent glass and transparent resin.

9. The photo-catalyzer according to claim 1, wherein said substrate is a porous support.

10. The photo-catalyzer according to claim 9, wherein said porous support is formed from a transparent material.

* * * * *